(12) United States Patent
Wakita et al.

(10) Patent No.: US 8,022,197 B2
(45) Date of Patent: Sep. 20, 2011

(54) NUCLEIC ACID AND GENE DERIVED FROM NOVEL HCV STRAIN AND REPLICON-REPLICATING CELL USING SAID GENE

(75) Inventors: Takaji Wakita, Tokyo (JP); Takanobu Kato, Aichi (JP); Tomoko Date, Kanagawa (JP); Michiko Miyamoto, Tokyo (JP)

(73) Assignees: Tokyo Metropolitan Organization for Medical Research, Tokyo (JP); Toray Industries Inc., Tokyo (JP)

( * ) Notice: Subject to any disclaimer, the term of this patent is extended or adjusted under 35 U.S.C. 154(b) by 1551 days.

(21) Appl. No.: 10/572,476

(22) PCT Filed: Sep. 16, 2004

(86) PCT No.: PCT/JP2004/014003
§ 371 (c)(1),
(2), (4) Date: Jul. 10, 2008

(87) PCT Pub. No.: WO2005/028652
PCT Pub. Date: Mar. 31, 2005

(65) Prior Publication Data
US 2009/0035747 A1 Feb. 5, 2009

(30) Foreign Application Priority Data
Sep. 19, 2003 (JP) .................................. 2003-329082

(51) Int. Cl.
*C07H 21/00* (2006.01)
*A61K 39/29* (2006.01)
(52) U.S. Cl. ................ 536/23.72; 424/228.1; 424/201.1
(58) Field of Classification Search ........................ None
See application file for complete search history.

(56) References Cited

U.S. PATENT DOCUMENTS

| 5,428,145 | A | 6/1995 | Okamoto et al. | |
| 6,630,343 | B1 | 10/2003 | Bartenshclager | |
| 7,659,103 | B2 * | 2/2010 | Wakita et al. | 435/235.1 |
| 2003/0009775 | A1 | 1/2003 | Glenn | |
| 2005/0250093 | A1 * | 11/2005 | Gates et al. | 435/5 |

FOREIGN PATENT DOCUMENTS

| JP | 6-121689 A | 5/1994 |
| JP | 2002-171978 A | 6/2002 |
| WO | WO-00/75337 A1 | 12/2000 |
| WO | WO-00/75338 A2 | 12/2000 |
| WO | WO-2004/044182 A2 | 5/2004 |

OTHER PUBLICATIONS

Kato, T. et al., J. Med. Virol. (2001), vol. 64, No. 3, pp. 334 to 339.
Genbank [online]; National Center for Bio technology Information, Bethesda MD, USA, [retrived on Dec. 15, 2004] Retrieved from the Internet: URL:http:www.ncbi.nlm.nih.gov:80/entrez/viewer.fcgi?list_uids=13122261>, Accession No. AB047639.
Genbank [online]; National Center for Bio technology Information, Bethesda MD, USA, [retrieved on Dec. 15, 2004], Retrieved from the Internet: URL:http://www.ncbi.nlm.nih.gov:80/entrez/viewer.fcgi?list_uids=13122273>, Accession No. AB047645.
Takanobu Kato, Japan Health Sciences Foundation, pp. 14 to 19, Figs.1 p. 18, 1993.
Lim et al., Virology, vol. 303, pp. 79-99, (2002).
Lechmann et al., Hepatology, pp. 417-423, (Aug. 2001).
Scholle et al., Journal of Virology, vol. 78 No. 3, pp. 1513-1524, (Feb. 2004).
Kimura et al., "Antibody-Free Virion Titer Greatly Differs Between Hepatitis C Virus Genotypes," Journal of Medical Virology, vol. 61, pp. 37-43, (2000).
Date et al., The Journal of Biological Chemistry, vol. 279, No. 21, pp. 22371-22376, 2004.
Hadlock et al., "Human Monclonal Antibodies That Inhibit Binding of Hepatitis C Virus E2 Protein to CD81 and Recognize Conserved Conformational Epitopes," Journal of Virology, vol. 74, No. 22, pp. 10407-10416 (Nov. 2000).
Sequence alignment, SEQ ID No. 12 and SEQ ID No. 2 from copending U.S. Appl. No. 11/898,468, Nov. 18, 2008.
Meunier et al., "Evidence for cross-genotype neutralization of hepatitis C virus pseudo-particles and enhancement of infectivity by apolipoprotein C1," Proceedings of the National Academy of Sciences, USA, vol. 102, No. 12, pp. 4560-4565 (Epub Mar. 2005).
Pietschmann et al., "Persistent and Transient Replication of Full-Length Hepatitis C Virus Genomes in Cell Culture," Journal of Virology, vol. 76, No. 8, pp. 4008-4021 (Apr. 2002).
Gottwein et al., "Robust Hepatitis C Genotype 3a Cell Culture Releasing Adapted Intergenotypic 3a/2a (S52/JFH1) Viruses," Gastroenterology, vol. 133, No. 5, pp. 1614-1626 (Nov. 2007).
Mateu et al., "Intragenotypic JFH1 based recombinant hepatitis C virus produces high levels of infectious particles but causes increased cell death," Virology, vol. 376, No. 2, pp. 397-407 (Epub May 2008).
Blanchard et al., "Hepatitis C Virus-Like Particle Morphogenesis," Journal of Virology, vol. 76, No. 8, pp. 4073-4079 (Apr. 2002).
GenBank AB 114136, "Hepatitis C virus replicon pSGR-JFH1 gene for neomysin resistance gene product, hepatitis C virus nonstructural protein, complete cds," (first available Jan. 2004).
Ciccarone et al., "pSFV1 Eukaryotic Expression Vector: A Novel Protein Expression System," Focus 15: 103-105, Life Technologies, Inc. (1993).
Date et al., "An infectious and selectable full-length replicon system with hepatitis C virus JFH-1 strain," Hepatology Research, vol. 37, No. 6, pp. 433-443 (Epub Apr. 2007).

(Continued)

*Primary Examiner* — Stacy B Chen
(74) *Attorney, Agent, or Firm* — Birch, Stewart, Kolasch and Birch, LLP

(57) ABSTRACT

The present invention relates to a gene derived from a novel fulminant hepatitis C virus strain, an HCV replicon RNA with a high replication efficiency obtained using the gene, and an HCV replicon-replicating cell transfected with the replicon RNA. When the HCV replicon RNA and the HCV replicon-replicating cell of the present invention are used, HCV proteins can be continuously produced in a large amount.

9 Claims, 2 Drawing Sheets
(1 of 2 Drawing Sheet(s) Filed in Color)

OTHER PUBLICATIONS

Database EMBL[online]; Feb. 25, 2001, Accession No. EM_VI:AB047644, XP002394805.
Kato, T. et al., J. Med. Virol. (2001), vol. 64, No. 3, pp. 334 to 339, XP-002986251.
Database EMBL[online]; Jan. 17, 2001, Accession No. EM_VI: AF169002, XP-002394806.
Kurihara C. et al., J. Med. Virol. (2001), vol. 64, pp. 466-475.
Database EMBL[online]; Jan. 17, 2001, Accession No. EM_PAT:AX057317, XP-002394807.
Kato, T. et al., Gastroenterology, (2003), vol. 125, No. 6, pp. 1808-1817, XP-002394801.
Simmonds P. et al., Hepatology, (May 1994), vol. 19, No. 5.
Choo, Q.L. et al., Science, vol. 244, (Apr. 21, 1989), pp. 359-362.
Kato, T. et al., J. Med. Virol., vol. 64, (2001), pp. 334-339.
Okamoto H. et al., J. of Gen. Virol., vol. 73, (1992), pp. 673-679.
Yoshioka K. et al., Hepatology, vol. 16, No. 2, (1992), pp. 293-299.
Mori S. et al., Biochemical and Biophysical Research Communication, vol. 183, No. 1, (Feb. 28, 1992), pp. 334-342.
Lohmann V. et al., Science, vol. 285, (Jul. 2, 1999), pp. 110-113.
Blight K. et al., Science, vol. 290, (Dec. 8, 2000), pp. 1972-1975.
Friebe, P., J. of Virol., vol. 75, No. 24, (Dec. 2001), pp. 12047-12057.
Ikeda M. et al., J. of Virol., vol. 76, No. 6, (Mar. 2002), pp. 2997-3006.

* cited by examiner

SEQUENCE LISTING

```
<160> NUMBER OF SEQ ID NOS: 8

<210> SEQ ID NO 1
<211> LENGTH: 6264
<212> TYPE: RNA
<213> ORGANISM: Hepatitis C virus
<220> FEATURE:
<223> OTHER INFORMATION: Inventor: Wakita, Takaji
        Inventor: Kato, Takanobu
        Inventor: Date, Tomoko

<400> SEQUENCE: 1
accauggcgc cuaucacugc uuaugcccag cagacacgag gccuauuggg cgccauagug      60
gugagcauga cgggccguga caagacagaa caggccgggg agauccaggu ccucuccaca     120
gucacucaaa ccuuccucgg gacuaccauc ucaggagucu gugggaccgu cuaccacggg     180
gcuggcaaca agacccuagc cggcucgcgg ggcccgguca cacagaugua cuccagcgcc     240
gagggagacu ugguagggug gcccaguccu cccgggacua aauccaugga gccgugcacg     300
ugcggagcgg ucgaccugua ccuggucacg cggaacgcug acgucauccc ggcucggaga     360
cgcggggaca agcggggagc guugcucucc ccgagaccuc ucucaacucu gaaggggucu     420 ucgggggggac cggugcucug ccccagggggc cacguuggucg ggaucuuccg ggcagccaua     480
ugcucgcggg gcguggccaa guccauagau uucauccccg uugaggcaau ugacaucguc     540
acgcgcuccc ccaccuuuac ugacaacagc acgccaccgg cugugcccca gaccuaucag     600
guuggauacu ugcacgcccc gacuggcagc gggaagagca ccaaaguccc ugucgcauau     660
gccgcccagg ggauaaaggu gcuagugcuc aaucccucug uggccgccac cuggggguuu     720
ggggcguacu uggccaaggc gcacggcauc aauccuaaca uuaggacugg agucaggacu     780
gugacgaccg gggaggcuau uacguauucc acguauggca aguuucucgc ugauggggc     840 ugcgcaggcg gcgccuauga caucaucaua ugcgaugagu gccaugccac ggaugcuacc     900
acccuucucg gcaucggaac aguucuugac caagcagagu cagcuggggu caggcuaacu     960
gugcuggcca cggcuacgcc ucccggauca auaacaaccc cucaccccaa cauagaggag    1020
guagcucucg gacaggaggg ugagauccc uucuugggga gagcgauccc ccuggccac     1080 aucaagggag ggaggcaccu gaucuucgc cacucgaaga aaaguguga cgagcucgcg     1140 gcggcccucc gggccauggg cuugaacgcu guggcauacu acagagggu ggacgucucc     1200 auaauaccag cucaaggaga cguggugguu gucgccacug acgcccucau gacagggguac     1260 acuggagacu uugaucccgu gauugacugc aacguagcgg uuacucaagu cguggacuuc     1320
agcuuggacc ccaccuucac cauuccacca caaaccgucc cccaagacgc cgucucacgc     1380
agccagcgcc gggggcgcac gggcagaggg agacuggggca uuuacaggua cguuuccacu     1440
```

```
ggugagcgag cuucgggaau guuugacagc guaacgcucu gcgagugcua cgaugcaggg   1500
gcugcauggu augaucucac accagcggaa accaccguca ggcuuagggc guauuucaac   1560
acgcccggcc ugcccgugug ccaagaccac cucgaguuuu gggaggcagu uuucaccggc   1620
cucacacaca uagaugccca cuaccuuucc caaacaaagc aagcggggga gaauuucgca   1680
uaccugacag ccuaucaggc cacagugugu gccagagcca agcccccucc cccgucuugg   1740
gacgucaugu ggaagugccu gacucgacuc aaacccacgc ucgugggccc cacaccucuc   1800 cguaccgcc uggguucagu uaccaacgau gucaccuuca cacaccugu gacaaaguac     1860 aucgcuacuu gcaugcaagc ugaccucgag gucaugacca gcacgugggu ccuagccggg   1920
ggaguccugg cugccaucgc cgcguacugc uuggcgacug ggugguguuc caucaucggc   1980
cguuugcacg ucaaccagcg aaccgucguu gcaccugaca aggagguccu cuaugaggcu   2040
uuugacgaga uggaggagug ugcuuccaga gcggcccuca uugaggaggc gcaacggaua   2100
gccgagaugc ugaagucuaa gauccaaggc uuauugcagc aggcuuccaa gcaggcccag   2160
gacauacaac caaccgugca ggcuucaugg cccaaggugg agcaauucug ggccaaacac   2220
auguggaacu cauuagcgg cauccaauau cuucgggac ugucaacgcu gccagggaac      2280
cccgcugugg ccucuaugau ggcauucagu gccgccauca ccaguccgcu gucgacuagc   2340
accaccaucc uucucaacau caugggaggc uggcuggcgu ucaaauugc gccaccgca      2400 ggggccacag gcuucguggu cagugggccug guggggggcug ccauaggcag cguaggcuug   2460
gguaaggugc uggugggacau cuuggcaggg uacggugcgg gcauuucggg ggcucucguc   2520
gcauucaaga ucaugucugg cgagaagccc uccauggagg augucaucaa ccugcugccc   2580
ggaauccugu ccccgggcgc ccuggugug gggucauuu gcgcggccau ucugcgccgu      2640
caugugggac cgggggaagg ugcgguccaa uggaugaaua ggcuuauugc cuuugcuucc    2700
agaggaaacc acgucgcccc cacccacuau gugacgagu cagaugcguc gcagcgcgug    2760
acccaacuac uuggcucucu caccauaacu agccugcuua gaaggcucca caauggauu     2820 acugaggacu gccccacccc augcaauggc ucauggcucc gcgaugugug gacugggug     2880 ugcaccaucc ugacugacuu uaaaaacugg cugaccucca aguugcccc aaagcugccc     2940 ggccucccu ucaucucuug ccaaagggg uauagggg cguagggccgg cacgggcauc       3000 auggucacg ggugcccuug uggcgccaac auuucggca augcccgcuu cggcucuaug      3060
agaaucacag ggccuaagac cugcaugaac accuggcagg ggacuuuccc uaucaacugc   3120 uacacgagg ccaaugcau gccgagaccu gcgccaaacu uuaagaccgc caucuggagg     3180
guggcggccu cagaguacgc ggaggugacg cggcacgggu cguacucuua cauaacaggg   3240
cugaccgcug acaaucugaa gguucccugc caaauaccau ucagagguu cuuuccugg     3300 guagacggag uacagaucca cagguuugcu cccacuccaa agccguucuu ucgggaugag   3360
gucucguuca gcgugggggcu caacucauuu guagucgggu ucagcuuccc cugcgacccu  3420
gaacccgacg cggacugguu gaugccaug cuaacagauc cuggccauau cacggcagag   3480
gcugcagcgc ggcgcuuagc gcggggguca ccccaucug aggcaagcuc ucagcaagc      3540 cagcugucgg cccgucgcu gcgugccacc ugugccaccc acggcacggc cuaugaugug    3600
gccauggugg augcuaaccu guucaugaag ggggaaguga uucggauaga guccgauucc   3660
aaaguggucg uucggacuc ucucgaccca cuggccgaag aggugagcga cgucgaaccc    3720
ucuauaccau cagaguacuu gauccccaag aaacaauucc caccagccuu gccggccugg   3780
gcgcggccug acuacaaccc accgcuugug gaaucgugga ggaagccuga cuaccaacca   3840
```

-continued

| | |
|---|---|
| cccacugucg cgggcugugc ucuccccccc cccaagaaga ccccgacgcc cccccccaagg | 3900 |
| aagcgucgga cggugagacu cagugagagc gccgugggag acauuccuca acagcuggcu | 3960 |
| auuaagaccu uuggccagcc cccuccaagc ggaggcccag accccccac ggggcgggc | 4020 |
| gccgccggcu ccggcgguca gacgcccccu gaugagccgg cuccuucgga gacggauucu | 4080 |
| gucccuucca ugcccccccu ugaggggag cccggagacc cagaccugga gcuuggccag | 4140 |
| guagagcccc aaccccccccc ccaggggggg gaggcggcuc ccgacucaga cucugggucg | 4200 |
| uggucuaccu gcuccgagga ggaggauucc accgugugcu gcuccaugcu auacuccugg | 4260 |
| accgggggccc uuauaacucc uugcagcccc gaagaggaga aguugccaau caaucccccug | 4320 |
| agcaacucau uguugcgcua ccacaacaag guguacugca cuacaucaag aagugcguca | 4380 |
| cugagggcca aaaagguaac uuuugacagg augcaaguac ucgaugccca cuaugacuca | 4440 |
| gucuuaaagg acauuaagcu agcggccucc aaggucagcg caaggucccu cagcuuggag | 4500 |
| gaggcgugca agcugacccc gccccacucu gcgaggucca aauauggauu uggggcuaag | 4560 |
| gagguccgca gcuuguccgg gagggccguc aaccacauca aguccgugug aaggaccuc | 4620 |
| uuggaagacu cacaaacacc aauaccuaca accaucaugg ccaagaauga gguguucugc | 4680 |
| gugaacccug cuaaggggg caagaaagca gcucgccuca ucguuuaccc cgaccuuggu | 4740 |
| gucagggucu gcgaaaagau ggcccucuau gauguugcac aaaagcuucc ucaggcggug | 4800 |
| augggggccu ccuaugggu ccaguacucu cccgcccagc ggguggaguu ucucuugaaa | 4860 |
| gcguggggcgg acaagaaaga cccuaugggu uuuucguaug aucccgaug cuuugacuca | 4920 |
| acugucacug agagagacau aagaacugag gaggacauau accugccugu cucccuacccc | 4980 |
| gaggaggccc gcacugccac acacucgcug acugagagac uuuacguggg agggcccaug | 5040 |
| uucaacagca agggccagac cugcgggcuac aggcguugcc gcgcuagcgg ggugcucacc | 5100 |
| acuagcaugg ggaauaccau cacaugcuau guaaaagccc uagcggccug caaggccgca | 5160 |
| gggauaguug caccccacgau gcuggauagc ggcgaugacu gguugucau ucagaaaagc | 5220 |
| caggggacug aggaggacga gcggaaccug agaccuucca cggaggcuau gaccagguau | 5280 |
| ucugccccuc cuggugaccc ccccagaccg gaauacgacu uggagcugau aacauccugc | 5340 |
| uccucaaaug ugucuguggc acuuggcccc cggggcaacc gcagauacua ucugaccaga | 5400 |
| gaccccacca cuccaaucgc ccgggcugcc ugggaaacag ucagacacuc cccugucaau | 5460 |
| ucauggcugg gaaacaucau ccaguacgcu ccaaccauau ggguucguau gguccugaug | 5520 |
| acacauuucu acuccauucu caauggccaa gacacucugg accagaaccu uaacuuugaa | 5580 |
| auguauggag cuguguacuc uguaagcccc uuggaccucc cagccauaau ugaaaagcuc | 5640 |
| caugggcuug acgcuucucu ucugcacaca uacucuccca acgaacugac gcgaguggcu | 5700 |
| ucagcccuca gaaaacuugg ggcgccacc cucagagcgu ggaagagccg ggcgcgugca | 5760 |
| gucagagcgu cccucaucuc ccguggaggg agacggccg ucugcggucg auaucucuuc | 5820 |
| aacugggcgg ugaagaccaa gcucaaacuc acuccauugc cggaggcgcg ccaucuggau | 5880 |
| uuauccaguu gguucaccgu cggcgccggc gggggcgaca uuuaucacag cgugucgcgu | 5940 |
| gcccgacccc gcuuguuacu ccuuagccua cuccuacucu uuguaggagu aggccuuuuc | 6000 |
| cuacuccccg cucgguagag cggcacacau uagcuacacu ccauagcuaa cuguuccauu | 6060 |
| uuuuuuuuuu uuuuuuuuuu uuuuuuuuuu uuuuuuuuuu uuuuuuuuuu uuuuuuuuuu | 6120 |
| cuuuuccuuc cuuucuuuuu cacuuuacuu cauucuuucc ugguggcucc aucuuagccc | 6180 |
| uagucacggc uagcugugaa agguccguga gccgcaugac ugcagagagu gccguaacug | 6240 |

-continued

| | |
|---|---|
| gucucucugc agaucauguc uaga | 6264 |

<210> SEQ ID NO 2
<211> LENGTH: 6018
<212> TYPE: RNA
<213> ORGANISM: Hepatitis C virus

<400> SEQUENCE: 2

| | |
|---|---|
| accauggcgc uaucacugc uuaugcccag cagacacgag gccuauuggg cgccauagug | 60 |
| gugagcauga cggccguga caagacagaa caggccgggg agauccaggu ccucuccaca | 120 |
| gucacucaaa ccuuccucgg gacuaccauc ucaggagucu guggaccgu cuaccacggg | 180 |
| gcuggcaaca agacccuagc cggcucgcgg ggcccgguca cacagaugua cuccagcgcc | 240 |
| gagggagacu gguaggggug gcccaguccu cccgggacua aauccaugga gccgugcacg | 300 |
| ugcggagcgg ucgaccugua ccggucacg cggaacgcug acgucauccc ggcucggaga | 360 |
| cgcggggaca agcggggagc guugcucucc ccgagaccuc ucuaacucu gaaggggucu | 420 |
| ucggggggac cggugcucug ccccaggggc acguugucg ggaucuuccg ggcagccaua | 480 |
| ugcucgcggg gcguggccaa guccauagau uucaucccg uugaggcaau ugacaucguc | 540 |
| acgcgcuccc ccaccuuuac ugacaacagc acgccaccgg cugugcccca gaccuaucag | 600 |
| guuggauacu ugcacgcccc gacuggcagc gggaagagca ccaaaguccc ugucgcauau | 660 |
| gccgcccagg gguauaaggu gcuagugcuc aaucccucgg uggccgccac cuuggggguu | 720 |
| ggggcguacu uggccaaggc gcacggcauc aauccaaca uuaggacugg agucaggacu | 780 |
| gugacgaccg gggaggcuau uacguauucc acguauggca aguuucucgc ugauggggc | 840 |
| ugcgcaggcg gcgccauga caucaucaua ugcgaugagu gccaugccac ggaugcuacc | 900 |
| acccuucucg gcaucggaac aguucuugac caagcagagu cagcuggggu caggcuaacu | 960 |
| gugcuggcca cggcuacgcc ucccggauca auaacaaccc cucaccccaa cauagaggag | 1020 |
| guagcucucg gacaggaggg ugagaucccc uucuauggga gagcgauccc ccuggccac | 1080 |
| aucaagggag ggaggcaccu gaucuucugc cacucgaaga aaaaguguga cgagcucgcg | 1140 |
| gcggccuccc gggccauggg cuugaacgcu guggcauacu acagagggu ggacgucucc | 1200 |
| auaauaccag cucaaggaga cguggugguu gucgccacug acgcccucau gacagggua | 1260 |
| acuggagacu uugacuccgu gauugacugc aacuagcgg uuacuaagu cguggacuuc | 1320 |
| agcuuggacc ccaccuucac cauauccaca caaaccgucc cccaagacgc cgucucacgc | 1380 |
| agccagcgcc gggggcgcac gggcagaggg agacugggca uuuacaggua cguuuccacu | 1440 |
| ggugagcgag cuucgggaau guuugacagc guaacgcucu gcgagugcua cgaugcaggg | 1500 |
| gcugcauggu augaucucac accagcgaaa accaccguca ggcuuagggc guauuucaac | 1560 |
| acgcccggcc ugcccgugug ccaagaccac cucgaguuuu gggaggcagu uucaccggc | 1620 |
| cucacacaca uagaugccca cuaccuuucc caaacaaagc aagcggggga gaauuucgca | 1680 |
| uaccugacag ccuaucaggc cacagugugu gccagagcca agccccucc cccgucuugg | 1740 |
| gacgucaugu ggaagugccu gacucgcacu aaacccacgc ucgugggccc cacaccucuc | 1800 |
| cuguaccgcc uggguucagu uaccaacgau gucaccuuca cacccugu gacaaaguac | 1860 |
| aucgcuacuu gcaugcaagc ugaccucgag ucaugaacca gcacguggu ccuagccggg | 1920 |
| ggauccuggg cugccaucgc cgcguacugc uuggcgacug ggugguguuc caucaucggc | 1980 |
| cguuugcacg ucaaccagcg aaccgucguu gcaccgaca aggagguccu cuaugaggcu | 2040 |
| uuugacgaga uggaggagug ugcuuccaga gcggcccuca ugaggaggc gcaacggaua | 2100 |

-continued

| | |
|---|---|
| gccgagaugc ugaagucuaa gauccaaggc uuauugcagc aggcuuccaa gcaggcccag | 2160 |
| gacauacaac caaccgugca ggcuucaugg cccaaggugg agcaauucug gccaaacac | 2220 |
| auguggaacu ucauuagcgg cauccaauau cuugcgggac ugucaacgcu gccagggaac | 2280 |
| cccgcugugg ccucuaugau ggcauucagu gccgccauca ccaguccgcu gucgacuagc | 2340 |
| accaccaucc uucucaacau caugggaggc uggcuggcgu cucaaauugc gccacccgca | 2400 |
| ggggccacag gcuucguggu caguggccug gugggggcug ccauaggcag cguaggcuug | 2460 |
| gguaaggugc ugguggacau cuuggcaggg uacggugcgg gcauucgggg ggcucucguc | 2520 |
| gcauucaaga ucaugucugg cgagaagccc uccauggagg augucaucaa ccugcugccc | 2580 |
| ggaauccugu ccccgggcgc ccugguggug ggggucauuu gcgcggccau ucugcgccgu | 2640 |
| caugugggac cggggggaagg ugcgguccaa uggaugaaua ggcuuauugc cuuugcuucc | 2700 |
| agaggaaacc acgucgcccc cacccacuau gugacggagu cagaugcguc gcagcgcgug | 2760 |
| acccaacuac uuggcucucu caccauaacu agccugcuua gaaggcucca caauuggauu | 2820 |
| acugaggacu gccccacccc augcaauggc ucauggcucc gcgaugugug ggacuggug | 2880 |
| ugcaccaucc ugacugacuu uaaaaacugg cugaccucca aguuguuccc aaagcugccc | 2940 |
| ggccucccccu ucaucucuug ccaaaagggg uauaggggcg acugggccgg cacgggcauc | 3000 |
| auggucacgc ggugcccuug uggcgccaac auuucuggca augccgcuu cggcucuaug | 3060 |
| agaaucacag ggccuaagac cugcaugaac accggcaggg gacuuuccc uaucaacugc | 3120 |
| uacacgaggg ccaaugcau gccgagaccu gcgccaaacu uuaagaccgc caucuggagg | 3180 |
| guggcggccu cagaguacgc ggaggugacg cggcacgggu cguacucuua cauaacaggg | 3240 |
| cugaccgcug acaaucugaa gguucccugc caaauaccau uccagaguu cuuuuccugg | 3300 |
| guagacggag uacagaucca cagguuugcu cccacuccaa agccguucuu ucgggaugag | 3360 |
| gucucguuca gcguggggcu caacucauuu guagucgggu cucagcuucc cugcgacccu | 3420 |
| gaacccgacg cggacguguu gaugugccau cuaacagauc cuggccauau cacggcagag | 3480 |
| gcugcagcgc ggcgcuuagc gcgggggguca ccccccaucug aggcaagcuc ucagcaagc | 3540 |
| cagcugucgg ccccgucgcu gcgugccacc ugugccaccc acggcacggc cuaugaugug | 3600 |
| gccauggugg augcuaaccu guucaugaag ggggaaguga uucggauaga guccgauucc | 3660 |
| aaagugucgu ucuggacuc ucucgaccca cuggccgaag aggugagcga cgucgaaccc | 3720 |
| ucuauaccau cagaguacuu gauccccaag aaacaauucc caccagccuu gccggccugg | 3780 |
| gcgcggccug acuacaaccc accgcuugug gaaucgugga ggaagccuga cuaccaacca | 3840 |
| cccacugucg cgggcugugc ucuccccccc cccaagaaga cccgacgcc cccccaagg | 3900 |
| aagcgucgga cggugagacu caguagagc gccguggag acauccucca acagcuggcu | 3960 |
| auuaagaccu uggccagcc cccuccaagc ggaggcccag acccccccac ggggcgggc | 4020 |
| gccgccggcu ccggcgguca gacgcccccu gaugagccgg cuccuucgga gacgauucu | 4080 |
| gucuccucca ugcccccccu ugagggggag cccggagacc agaccuggga gcuuggccag | 4140 |
| guagagcccaa acccccccc ccaggggggg gaggcggcuc ccgacucaga cucugggucg | 4200 |
| uggucuaccu gcuccgagga ggaggauucc accgugugcu gcuccauguc auacuccugg | 4260 |
| accgggccccc uuauaacucc uugcagcccc gaagaggaga aguugccaau caaucccccug | 4320 |
| agcaacucau uguugcgcua ccacaacaag guguacugca cuacaucaag aagugcguca | 4380 |
| cugagggcca aaaaggguaac uuuugacagg augcaaguac ucgaugccca cuaugacuca | 4440 |
| gucuuaaagg acauuaagcu agcggccucc aaggucagcg caaggucccu cagcuuggag | 4500 |

```
gaggcgugca agcugacccc gccccacucu gcgaggucca aauauggauu uggggcuaag      4560
gagguccgca gcuugccgg gagggccguc aaccacauca aguccgugug aaggaccuc       4620 uuggaagacu cacaaacacc aauaccuaca accaucaugg ccaagaauga gguguucugc     4680
gugaacccug cuaaggggg caagaaagca gcucgccuca ucguuuaccc cgaccuuggu      4740 gucaggucu gcgaaaagau ggcccucuau gauguugcac aaaagcuucc ucaggcggug      4800 auggggccu ccuaugggu ccaguacucu cccgcccagc ggguggaguu ucucuugaaa       4860
gcgugggcgg acaagaaaga cccuaugggu uuucguaug auacccgaug cuuugacuca      4920
acugucacug agagagacau aagaacugag gaggacauau accugccug cucccuaccc      4980 gaggaggccc gcacugccac acacucgcug acgagagac uuuacgugg agggcccaug       5040 uucaacagca agggccagac cugcggguac aggcguugcc cgcuagcgg ggugcucacc     5100 acuagcaugg ggaauaccau cacaugcuau guaaaagccc uagcggccug caaggccgca    5160
gggauaguug cacccacgau gcugguaugc ggcgaugacu ugguugucau ucagaaaagc    5220
caggggacug aggaggacga gcggaaccug agagccuuca cggaggcuau gaccagguau    5280 ucugcccuc cugugacccc cccagaccg gaauacgacu uggagcugau aacauccugc      5340
uccucaaaug ugucugugc acuuggcccc cggggcaacc gcagauacua ucugaccaga    5400
gaccccacca cuccaaucgc ccgggcugcc ugggaaacag ucagacacuc cccugucaau   5460
ucauggcugg gaaacaucau ccaguacgcu ccaaccauau ggguucguau gguccugaug   5520
acacauuucu acuccauucu cauggcccaa gacacucugg accagaaccu uaacuuugaa   5580
auguauggag cuguguacuc uguaagcccc uuggaccucc cagccauaau ugaaaagcuc   5640
caugggcuug acgcuuucuc ucugcacaca uacucucca cgaacugac gcgaguggcu    5700 ucagcccuca gaaacuuggg ggcgccaccc cucagagcgu ggaagagccg ggcgcguca    5760 gucagagcgu ccccucaucuc ccguggagg agagcggccg ucugcggucg auaucucuuc   5820
aacugggcgg ugaagaccaa gcucaaacuc acuccauugc cggaggcgcg ccaucggau    5880 uuauccaguu gguucaccgu cggcgccggc gggggcgaca uuuaucacag cgugucgcgu   5940
gcccgacccc gcuuguuacu ccuuagccua cuccuacucu uguaggagu aggccuuuuc   6000 cuacucccg cucgguag                                                  6018

<210> SEQ ID NO 3
<211> LENGTH: 340
<212> TYPE: RNA
<213> ORGANISM: Hepatitis C virus

<400> SEQUENCE: 3
acccgccccu aauaggggcg acacuccgcc augaaucacu ccccugugag gaacuacugu     60
cuucacgcag aaagcgucua gccauggcgu uaguaugagu gucguacagc cuccaggccc    120
cccccucccg ggagagccau aguggucugc ggaaccggug aguacaccgg aauugccggg    180
aagacugggu ccuuucuugg auaaacccac ucuaugcccg ccauuuggg cgugccccg      240 caagacugcu agccgaguag cguuggguug cgaaaggccu uguggaacug ccugauaggg    300
ugcuugcgag ugccccggga ggucucguag accgugcauc                          340

<210> SEQ ID NO 4
<211> LENGTH: 241
<212> TYPE: RNA
<213> ORGANISM: Hepatitis C virus

<400> SEQUENCE: 4
```

| | |
|---|---:|
| agcggcacac auuagcuaca cuccauagcu aacuguucca uuuuuuuuuu uuuuuuuuuu | 60 |
| uuuuuuuuuu uuuuuuuuuu uuuuuuuuuu uuuuuuuuuu uucuuuuccu uccuuucuuu | 120 |
| uucacuuuac uucauucuuu ccugguggcu ccaucuuagc ccagucacg gcuagcugug | 180 |
| aaagguccgu gagccgcaug acugcagaga gugccguaac uggucucucu gcagaucaug | 240 |
| u | 241 |

<210> SEQ ID NO 5
<211> LENGTH: 340
<212> TYPE: RNA
<213> ORGANISM: Hepatitis C virus

<400> SEQUENCE: 5

| | |
|---|---:|
| acccgccccu aauaggggcg acacuccgcc augaaucacu ccccugugag gaacuacugu | 60 |
| cuucacgcag aaagcgucua gccauggcgu uaguaugagu gucguacagc cuccaggccc | 120 |
| cccccucccg ggagagccau aguggucugc ggaaccggug aguacaccgg aauugccggg | 180 |
| aagacugggu ccuuucuugg auaaacccac ucuaugcccg gccauuuggg cgugccccg | 240 |
| caagacugcu agccgaguag cguuggguug cgaaaggccu uguggacug ccugauaggg | 300 |
| ugcuugcgag ugccccggga ggucucguag accgugcauc | 340 |

<210> SEQ ID NO 6
<211> LENGTH: 241
<212> TYPE: RNA
<213> ORGANISM: Hepatitis C virus

<400> SEQUENCE: 6

| | |
|---|---:|
| agcggcacac auuagcuaca cuccauagcu aacuguucca uuuuuuuuuu uuuuuuuuuu | 60 |
| uuuuuuuuuu uuuuuuuuuu uuuuuuuuuu uuuuuuuuuu uucuuuuccu uccuuucuuu | 120 |
| uucacuuuac uucauucuuu ccugguggcu ccaucuuagc ccagucacg gcuagcugug | 180 |
| aaagguccgu gagccgcaug acugcagaga gugccguaac uggucucucu gcagaucaug | 240 |
| u | 241 |

<210> SEQ ID NO 7
<211> LENGTH: 8029
<212> TYPE: RNA
<213> ORGANISM: Artificial Sequence
<220> FEATURE:
<223> OTHER INFORMATION: Description of Artificial Sequence:JFH2.1
      replicon RNA

<400> SEQUENCE: 7

| | |
|---|---:|
| acccgccccu aauaggggcg acacuccgcc augaaucacu ccccugugag gaacuacugu | 60 |
| cuucacgcag aaagcgucua gccauggcgu uaguaugagu gucguacagc cuccaggccc | 120 |
| cccccucccg ggagagccau aguggucugc ggaaccggug aguacaccgg aauugccggg | 180 |
| aagacugggu ccuuucuugg auaaacccac ucuaugcccg gccauuuggg cgugccccg | 240 |
| caagacugcu agccgaguag cguuggguug cgaaaggccu uguggacug ccugauaggg | 300 |
| ugcuugcgag ugccccggga ggucucguag accgugcauc augagcacaa aucccaaacc | 360 |
| ucaaagaaaa accaacagaa acaccaaccg ucgcccaaug auugaacaag auggauugca | 420 |
| cgcagguucu ccggccgcuu ggguggagag gcuauucggc uaugacuggg cacaacagac | 480 |
| aaucggcugc ucugaugccg ccguguuccg gcugucagc caggggcgcc cgguucuuuu | 540 |
| ugucaagacc gaccuguccg gugcccugaa ugaacgcag gacgaggcag cgcggcuauc | 600 |
| guggcuggcc acgacgggcg uuccuugcgc agcugugcuc gacguuguca cugaagcggg | 660 |

```
aagggacugg cugcuauugg gcgaagugcc ggggcaggau cuccugucau cucaccuugc    720
uccugccgag aaaguaucca ucauggcuga ugcaaugcgg cggcugcaua cgcuugaucc    780
ggcuaccugc ccauucgacc accaagcgaa acaucgcauc gagcgagcac guacucggau    840
ggaagccggu cuugucgauc aggaugaucu ggacgaagag caucaggggc ucgcgccagc    900
cgaacuguuc gccaggcuca aggcgcgcau gcccgacggc gaggaucucg ucgugaccca    960
uggcgaugcc ugcuugccga auaucauggu ggaaaauggc cgcuuuucug gauucaucga   1020
cuguggccgg cugggugugg cggaccgcua ucaggacaua gcguuggcua cccgugauau   1080
ugcugaagag cuuggcggcg aaugggcuga ccgcuuccuc gugcuuuacg guaucgccgc   1140
ucccgauucg cagcgcaucg ccuucuaucg ccucuugac gaguucuucu gaguuuaaac    1200
ccucucccuc cccccccccu aacguuacug gccgaagccg cuuggaauaa ggccggugug   1260
cguuugucua uauguuauuu uccaccauau ugccgucuuu uggcaaugug agggcccgga   1320
aaccuggccc ugucuucuug acgagcauuc cuaggggucu uccccucuc gccaaaggaa    1380 ugcaaggucu guugaauguc gugaaggaag caguccucu ggaagcuucu ugaagacaaa    1440
caacgucugu agcgacccuu ugcaggcagc ggaaccccc accugcgac aggugccucu     1500 gcggccaaaa gccacgugua uaagauacac cugcaaaggc ggcacaaccc cagugccacg   1560
uugugaguug gauaguugug gaaagaguca aauggcucuc cucaagcgua uucaacaagg   1620
ggcugaagga ugcccagaag guaccccauu guagggauc ugaucugggg ccucggugca    1680
caugcuuuac auguguuuag ucgagguuaa aaaaacgucu aggccccccg aaccacgggg   1740 acguggguuuu ccuuugaaaa acacgaugau accauggcgc cuaucacugc uuaugcccag  1800
cagacacgag gccuauuggg cgccauagug gugagcauga cgggccguga caagacagaa   1860
caggccgggg agauccaggu ccucuccaca gucacucaaa ccuuccucgg gacuaccauc   1920
ucaggagucu uguggaccgu cuaccacggg gcuggcaaca agaccccuagc cggcucgcgg  1980 ggcccgguca cacagaugua cuccagcgcc gagggagacu gguaggguug cccagugccu   2040
cccgggacua aauccaugga gccgugcacg ugccgagcgg ucgaccugua ccuggucacg   2100
cggaacgcug acgucauccc ggcucggaga gcgggggaca agcggggagc guugcucucc   2160
ccgagaccuc ucucaacucu gaaggggucu ucgggggggac cggugcucug ccccaggggc   2220
cacguugucg ggaucuuccg ggcagccaua ugcucgcggg gcguggccaa guccauagau   2280
uucauccccg uugaggcaau ugacaucguc acgcgcuccc ccaccuuuac ugacaacagc   2340
acgccaccgg cugugcccca gaccuaucag guuggauacu ugcacgcccc gacuggcagc   2400
gggaagagca ccaaagugcc cugucgcauau gccgcccagg gguauaaggu gcuagugcuc   2460
aaucccucgg uggccgccac cuuggggguu ggggcguacu uggccaaggc gcacggcauc   2520
aauccuaaca uuaggacugg agucaggacu gugacgaccg gggaggcuau uacguauucc   2580
acguauggca aguuucucgc ugauggggc ugcgcaggcg gcgccauga caucaucaua     2640 ugcgaugagu ccaugccac ggaugcuacc acccuucucg gcaucggaac aguucuugac    2700
caagcagagu cagcugggu caggcuaacu gugcuggcca cggcuacgcc ucccggauca    2760
auaacaaccc cucacccccaa cauagaggag guagcucucg gacaggaggg ugagaucccc  2820
uucuagggga gagcgaucc ccuggcccac aucaaggag gaaggcaccu gaucuucugc     2880
cacucgaaga aaaagucuga cgagcucgcg gcggcccucc gggccauggg cuugaacgcu   2940
guggcauacu acagagggu ggacgucucc auaauaccag cucaaggaga cguggugguu    3000
gucgccacug acgcccucau gacaggguac acuggagacu uugacuccgu gauugacugc   3060
```

```
aacguagcgg uuacucaagu cguggacuuc agcuuggacc ccaccuucac cauauccaca    3120
caaaccgucc cccaagacgc cgucucacgc agccagcgcc gggggcgcac gggcagaggg    3180
agacugggca uuuacaggua cguuuccacu ggugagcgag cuucgggaau guuugacagc    3240
guaacgcucu gcgagugcua cgaugcaggg gcugcauggu augaucucac accagcggaa    3300
accaccguca ggcuuagggc guauuucaac acgcccggcc ugcccgugug ccaagaccac    3360
cucgaguuuu gggaggcagu uuucaccggc ucacacaca uagaugccca cuaccuuucc    3420
caaacaaagc aagcggggga gaauuucgca uaccugacag ccuaucaggc cacagugugu    3480
gccagagcca agcccaucc cccgucuugg gacgucaugu ggaagugccu gacucgacuc    3540
aaacccacgc ucgugggccc cacaccucuc cuguaccgcc ugguucagu uaccaacgau    3600 gucaccuuca cacacccugu gacaaaguac aucgcuacuu gcaugcaagc ugaccucgag    3660
gucaugacca gcacgugggu ccuagccggg ggaguccugg cugccaucgc cgcguacugc    3720
uuggcgacug ggugguguuc caucaucggc cguuugcacg ucaaccagcg aaccgucguu    3780
gcaccugaca aggagguccu cuaugaggcu uuugacgaga uggaggagug ugcuuccaga    3840
gcggcccuca uugaggaggc gcaacggaua gccgagaugc ugaagucuaa gauccaaggc    3900
uuauugcagc aggcuuccaa gcaggcccag gacauacaac caaccgugca ggcuucaugg    3960
cccaaggugg agcaauucug ggccaaacac auguggaacu cauuagcgg cauccaauau    4020 cuugcgggac ugucaacgcu gccagggaac cccgcugugg ccucuaugau ggcauucagu    4080
gccgccauca ccaguccgcu gucgacuagc accaccaucc uucucaacau cauggggaggc    4140 uggcuggcgu cucaaauugc gccacccgca ggggccacag gcuucguggu cagugccug    4200 guggggcug ccauaggcag cguaggcuug gguaaggug uggugacau cuggcaggg    4260 uacgugcgg gcauuucggg ggcucucguc gcaucaaga ucaugucugg cgagaagccc    4320
uccauggagg augucaucaa ccugcugccc ggaauccugu cccgggcgc ccuggugug    4380 ggggucauuu gcgcggccau ucugcgccgu caugugggac cggggaagg ugcgguccaa    4440 uggaugaaua ggcuuauugc cuuugcuucc agaggaaacc acgucgcccc cacccacuau    4500
gugacggagu cagaugcguc gcagcgcgug acccaacuac uuggcucucu caccauaacu    4560
agccugcuua gaaggcucca caauuggauu acugaggacu gccccacccc augcaauggc    4620
ucauggcucc gcgaugugug ggacgggug ugcaccaucc ugacugacuu uaaaaacugg    4680
cugaccucca aguuguccc aaagcugccc ggccucccu ucaucucuug ccaaaagggg    4740
uauaggggcg acugggccgg cacgggcauc augguccacg ggugcccuug uggcgccaac    4800
auuucuggca auguccgcuu cggcucuaug agaaucacag ggccuaagac cugcaugaac    4860
accuggcagg ggacuuuccc uaucaacugc uacacggagg ccaaugcau ccgagaccu    4920 gcgccaaacu uuaagaccgc caucuggagg guggcggccu cagauacgc ggaggugacg    4980 cggcacgggu cguacucuua cauaacaggg cugaccgcug acaaucgaa gguucccugc    5040 caaauaccau cuccagaguu cuuuccuugg guagacggag uacagaucca caggquuugcu    5100 cccacuccaa agccguucuu ucgggaugag gucucgguuca gcgugggcu caacucauuu    5160 guagucgggu cucagcuucc cugcgacccu gaaccgacg cggacguguu gaugccaug    5220 cuaacagauc cuggccauau cacggcagag gcugcagcgc ggcgcuuagc gcgggguca    5280 cccccaucug aggcaagcuc ucagcaagc cagcugucgg cccgucgcu gcgugccacc    5340 ugugccaccc acggcacggc cuaugaugug gccaugggug augcuaaccu guucaugaag    5400
ggggaaguga uucggauaga guccgauucc aaagugguc uucuggacuc ucucgaccca    5460
```

```
cuggccgaag aggugagcga cgucgaaccc ucuauaccau cagaguacuu gaucccaag    5520 aaacaauucc caccagccuu gccggccugg gcgcggccug acuacaaccc accgcuugug    5580
gaaucgugga ggaagccuga cuaccaacca cccacugucg cgggcugugc ucucccccc     5640 cccaagaaga ccccgacgcc ccccccaagg aagcgucgga cggugagacu cagugagagc    5700
gccgugggag acauccucca acagcuggcu auuaagaccu uuggccagcc cccuccaagc    5760
ggaggcccag accccccac ggggggcgggc gccgccggcu ccggcgguca gacgccccu     5820 gaugagccgg cuccuucgga gacggauucu gucuccucca ugccccccu ugaggggag      5880 cccggagacc cagaccugga gcuuggccag guagagcccc aacccccccc ccagggggg     5940 gaggcggcuc ccgacucaga cucugggucg uggucuaccu gcccgagga ggaggauucc     6000 accgugugcu gcuccaugucu auacuccugg accggggccc uuauaacucc uugcagcccc   6060
gaagaggaga aguugccaau caaucccccug agcaacucau guuugcgcua ccacaacaag   6120
guguacugca cuacaucaag aagugcguca cugagggcca aaaagguaac uuugacagg     6180 augcaaguac ucgaugccca cuaugacuca gucuuaaagg acauuaagcu agcggccucc    6240
aaggucagcg caaggucccu cagcuuggag gaggcgugca agcugacccc gcccacucu    6300 gcgaggucca aauauggauu uggggcuaag gagguccgca gcuuguccgg gagggccguc    6360
aaccacauca aguccgugug gaggaccuc uuggaagacu cacaaacacc aauaccuaca    6420
accaucaugg ccaagaauga ggugucugc gugaacccug cuaaggggg caagaaagca    6480 gcucgccuca ucguuuaccc cgaccuuggu gucagggucu gcgaaaagau ggcccucuau   6540
gauguugcac aaaagcuucc ucaggcggug augggggccu ccuauggguu ccaguacucu   6600
cccgcccagc ggguggaguu ucucuugaaa gcgguggcgg acaagaaaga cccuaugggu   6660
uuuucguaug auacccgaug cuuugacuca acugucacug agagagacau aagaacugag   6720
gaggacauau accguccuug cucccuaccc gaggaggccc gcacgccac acacucgcug    6780 acugagagac uuuacguggg aggggcccaug uucaacagca agggccagac cugcggguac   6840
aggcguugcc gcgcuagcgg ggugcucacc acuagcaugg ggaauaccau cacaugcuau   6900
guaaaagccc uagcggccug caaggccgca gggauaguug cacccacgau gcuggauugc   6960
ggcgaugacu ugguugucau ucagaaaagc caggggacug aggagacga gcggaaccug    7020 agagccuuca cggaggcuau gaccagguau ucugcccuc cuggugaccc cccagaccg    7080 gaauacgacu uggagcugau aacaucucugc uccucaaaug ugucuggc acuuggcccc    7140 cggggcaacc gcagauacua ucugaccaga gaccccacca cuccaaucgc ccgggcugcc   7200
ugggaaacag ucagacacuc cccugucaau caugguucgg gaaacaucau ccaguacgcu   7260
ccaaccauau ggguucguau ggccugaug acacauuucu acuccauucu caugccccaa   7320
gacacucugg accagaaccu uaacuuugaa auguauggag cuguacucu guuaagcccc    7380 uuggaccucc cagccauaau ugaaaagcuc caugggcuug acgcuuucuc ucugcacaca   7440
uacucuccca cgaacugac gcgaguggcu cagcccucca gaaacuuggg gcgccacccc   7500
cucagagcgu ggaagagccg ggcgcgugca gucagagcgu cccucaucuc ccguggaggg   7560
agagcggccg ucugcggucg auaucucuuc aacugggcgg ugaagaccaa gcucaaacuc   7620
acuccauugc cggaggcgcg ccaucuggau uuaccaguu ggcuuaccgu cggccccggc    7680 ggggcgaca uuuaucacag cgucgcgcgu gcccgacccc gcuuguuacu ccuuagccua    7740
cuccuacucu uuguaggagu aggccuuuuc cuacuccccg cucggauagag cgcacacau    7800 uagcuacacu ccauagcuaa cuguucauu uuuuuuuuuu uuuuuuuuuu uuuuuuuuu     7860
```

| | | |
|---|---|---|
| uuuuuuuuuu uuuuuuuuuu uuuuuuuuuu cuuuuccuuc cuuucuuuuu cacuuuacuu | 7920 | |
| cauucuuucc ugguggcucc aucuuagccc uagucacggc uagcugugaa aggaccguga | 7980 | |
| gccgcaugac ugcagagagu gccguaacug gucucucugc agaucaugu | 8029 | |

<210> SEQ ID NO 8
<211> LENGTH: 6322
<212> TYPE: RNA
<213> ORGANISM: Artificial Sequence
<220> FEATURE:
<223> OTHER INFORMATION: Description of Artificial Sequence:JFH2.2
    replicon RNA

<400> SEQUENCE: 8

| | | |
|---|---|---|
| acccgcccca aagggcgac acccgccaga acaccccgg aggaacacgc cacgcagaaa | 60 | |
| gcgcagccag gcgagagagg cgacagcccc aggccccccc ccccgggaga gccaagggcg | 120 | |
| cggaaccggg agacaccgga agccgggaag acgggcccgg aaaacccacc agcccggcca | 180 | |
| gggcggcccc cgcaagacgc agccgagagc gggggcgaaa ggccgggacg ccgaaggggc | 240 | |
| gcgaggcccc gggaggccga gaccggcaca gagcacaaac ccaaacccaa agaaaaacca | 300 | |
| acagaaacac caaccgcgcc aagagaaca agaggagcac gcaggcccgg ccgcggggga | 360 | |
| gaggcacggc agacgggcac aacagacaac ggcgccgagc cgccggccgg cgcagcgcag | 420 | |
| gggcgcccgg cgcaagaccg accgccgggc ccgaagaacg caggacgagg cagcgcggca | 480 | |
| cgggcggcca cgacgggcgc cgcgcagcgg ccgacggcac gaagcgggaa gggacggcgc | 540 | |
| agggcgaagg ccggggcagg acccgcacca ccgcccgccg agaaagacca caggcgagca | 600 | |
| agcggcggcg caacgcgacc ggcaccgccc acgaccacca agcgaaacac gcacgagcga | 660 | |
| gcacgaccgg aggaagccgg cgcgacagga gacggacgaa gagcacaggg gccgcgccag | 720 | |
| ccgaacgcgc caggccaagg cgcgcagccc gacggcgagg accgcggacc caggcgagcc | 780 | |
| gcgccgaaaac aggggaaaag gccgccggac acgacgggcc ggcgggggc ggaccgcaca | 840 | |
| ggacaagcgg gcacccggaa gcgaagacg gcggcgaagg gcgaccgccc ggcacggac | 900 | |
| gccgccccga cgcagcgcac gcccacgccc gacgagccga gaaacccccc ccccccccc | 960 | |
| caacgacggc cgaagccgcg gaaaaggccg gggcggcaag accaccaagc gcgggcaagg | 1020 | |
| agggcccgga aaccggcccg ccgacgagca ccaggggccc cccgccaaa ggaagcaagg | 1080 | |
| cggaagcgga aggaagcagc ccggaagccg aagacaaaca acgcgagcga cccgcaggca | 1140 | |
| gcggaacccc ccaccggcga cagggcccgc ggccaaaagc cacggaaaga acaccgcaaa | 1200 | |
| ggcggcacaa ccccaggcca cggagggaa ggggaaagag caaaggcccc caagcgacaa | 1260 | |
| caaggggcga aggagcccag aaggacccca gagggacgca ggggcccggg cacagcacag | 1320 | |
| gagcgaggaa aaaacgcag gcccccgaa ccacggggac gggccgaaaa acacgagaac | 1380 | |
| aggcgccaca cgcagcccag cagacacgag gccagggcgc caaggggagc agacgggccg | 1440 | |
| gacaagacag aacaggccgg ggagaccagg ccccacagc accaaacccc cgggacacca | 1500 | |
| ccaggagcgg gaccgcacca cggggcggca acaagaccca gccggccgcg ggcccggca | 1560 | |
| cacagagacc cagcgccgag ggagacggag ggggcccagc ccccgggaca aaccaggagc | 1620 | |
| cggcacggcg gagcggcgac cgaccggcac gcgaacgcg acgcacccgg ccggagacgc | 1680 | |
| ggggacaagc ggggagcggc ccccgagac ccccgaccga aggggcccag ggggaccggg | 1740 | |
| cgccccaggg gccacgggg acccgggcag ccaagcccgg ggcggccaa gccaagacca | 1800 | |
| ccccggagag cgacacgcac gcgcccccca ccaccgacaa cagcacgcca ccggcggccc | 1860 | |

```
cagaccacag gggaaccgca cgccccaacc ggcagcggga agagcaccaa ggcccggcaa    1920
cgccgcccag gggacaaaga caggcgaacc ccggggcggc cacccggggc ggggcaacgg    1980
ccaaggcaca ggcacaaccc aaaaggacgg agcaggacgg acgacgggga ggccacacga    2040
cccacgaggc aagcccgccg aggggcggc aggcggcgcc agacacacaa gcgagaagcc     2100
acgccacgga cgcaccaccc ccggcacgga acagcgacca agcagagcag cggggcaggc    2160
aacggcggcc acggcacgcc cccggacaaa acaaccccca ccccaacaag aggaggagcc    2220
cggacaggag gggagacccc cagggagagc gaccccggc ccacacaagg agggaggca      2280 ccgaccgcca ccgaagaaaa agggacgagc cgcggcggcc cccgggccag ggcgaacgcg    2340
ggcaacacag aggggacgc ccaaaaccag ccaaggagac gggggcgcc acgacgcccc      2400 agacagggac acgagacga cccggagacg caacagcggg accaagcggg accagcggac    2460
cccacccacc aaccacacaa accgccccca agacgccgcc acgcagccag cgccggggc     2520 gcacgggcag agggagacgg gcaacaggac gccacgggag cgagccggga aggacagcga    2580
acgccgcgag gcacgagcag gggcgcagga gaccacacca gcggaaacca ccgcaggcag    2640
ggcgacaaca cgcccggccg ccgggcccaa gaccacccga ggggaggcag caccggccca    2700
cacacaagag cccacacccc caaacaaagc aagcggggga gaacgcaacc gacagccaca    2760
ggccacaggg gccagagcca aagccccccc ccgcgggacg cagggaaggc cgaccgacca    2820
aacccacgcc ggggccccac accccgacc gccggggcaga ccaacgagca cccacacacc    2880
cggacaaaga cacgcacgca gcaagcgacc cgaggcagac cagcacgggg ccagccgggg    2940
gagccggcgc cacgccgcga cgcggcgacg ggggccacac ggccggcacg caaccagcga    3000
accgcggcac cgacaaggag gcccagaggc gacgagagga ggagggccca gagcggcccc    3060
agaggaggcg caacggaagc cgagagcgaa gcaagaccaa ggcagcagca ggcccaagca    3120
ggcccaggac aacaaccaac cggcaggcca ggcccaaggg gagcaacggg ccaaacacag    3180
ggaaccaagc ggcaccaaac gcgggacgca acgcgccagg gaaccccgcg ggcccagagg    3240
cacaggccgc cacaccagcc gcgcgacagc accaccaccc caacacaggg aggcggcggc    3300
gccaaagcgc caccccgcagg ggccacaggc cgggcagggc cgggggggcg ccaaggcagc    3360
gaggcgggaa gggcggggac acggcaggga cgggcgggca cggggggcccg cgcacaagac    3420 agcggcgaga agccccaggc aggagcacaa ccgcgcccgg aaccgccccg ggcgcccggg    3480 gggggcagc gcggccacgc gccgcagggg accgggggaa gggcggccaa ggagaaaggc     3540
agccgcccag aggaaaccac gcgcccccac ccacaggacg gagcagagcg cgcagcgcgg    3600
acccaacacg gccccaccaa acagccgcag aaggcccaca aggaacgagg acgccccacc    3660
ccagcaaggc caggcccgcg aggggacgg gggcaccacc gacgacaaaa acggcgaccc    3720
caaggcccaa agcgcccggc cccccaccg ccaaaagggg aaggggcgac gggccggcac    3780
gggcacaggc acgcgggccc gggcgccaac acggcaagcc gccggccaga gaacacaggg    3840
ccaagaccgc agaacaccgg caggggaccc cacaacgcac acgagggcc aagcagccga    3900 gaccgcgcca aacaagaccg ccacggaggg ggcggcccag agacgcggag ggacgcggca    3960
cgggcgacca caaacagggc gaccgcgaca acgaaggccc gccaaaacca cccagagccc    4020
gggagacgga gacagaccac agggcccac ccaaagccgc cggagaggc cgcagcgggg     4080 gccaaccaga gcgggccagc cccgcgaccc gaacccgacg cggacgggag ccagcaacag    4140
accggccaac acggcagagg cgcagcgcgg cgcagcgcgg gggcacccc acgaggcaag    4200 ccccagcaag ccagcgcggc cccgcgcgcg gccaccggcc acccacggca cggccagagg    4260
```

```
gccaggggag caaccgcaga aggggggaagg acggaagagc cgaccaaagg gcgcggaccc    4320
cgacccacgg ccgaagaggg agcgacgcga acccccaacca cagagacgac cccaagaaac    4380
aacccaccag ccgccggccg ggcgcggccg acacaaccca ccgcgggaac gggaggaagc    4440
cgacaccaac cacccacgcg cggggcggcc ccccccccca agaagacccc gacgcccccc    4500
ccaaggaagc gcggacggga gaccaggaga gcgccggga gacacccaa cagcggcaaa     4560
gaccggccag cccccccaag cggaggccca gaccccccca cggggcggg cgccgccggc     4620
ccggcggcag acgccccga gagccggccc cggagacgga cgcccccagc cccccgagg      4680
gggagcccga gacccagac cggagcggcc aggagagccc caaccccccc cccaggggg      4740
ggaggcggcc ccgaccagac cgggcgggca ccgcccgagg aggaggacca ccgggcgccc    4800
agcaaccccgg accggggccc aaacccgcag ccccgaagag gagaaggcca acaacccga   4860
gcaaccaggc gcaccacaac aagggacgca cacacaagaa ggcgcacgag ggccaaaaag    4920
gaacgacagg agcaagaccg agcccacaga ccagcaaagg acaaagcagc ggccccaagg    4980
cagcgcaagg ccccagcgga ggaggcggca agcgacccg ccccaccgcg aggccaaaag    5040
gaggggcaag gaggccgcag cgccgggagg gccgcaacca cacaagcgg ggaaggaccc     5100
ggaagaccac aaacaccaaa ccacaaccac aggccaagaa gagggcgcgg aacccgcaag    5160
ggggcaaga aagcagccgc ccacgacccc gaccgggcag ggcgcgaaaa gaggccccag    5220
aggcacaaaa gccccaggcg ggaggggcc ccagggccag accccgccc agcggggag     5280
ccgaaagcgg ggcggacaag aaagaccag ggcgagaacc cgagcgacca acgcacgaga    5340
gagacaaaga acgaggagga caaaccgccg ccccacccga ggaggcccgc acgccacaca    5400
ccgcgacgag agacacgggg agggcccagc aacagcaagg gccagaccgc gggacaggcg    5460
gccgcgcagc gggggccacc acagcagggg aaaccacaca gcagaaaagc ccagcggccg    5520
caaggccgca gggaaggcac ccacgagcgg agcggcgaga cgggcaccag aaagccaggg    5580
gacgaggagg acgagcggaa ccgagagccc acggaggcag accaggacgc ccccccggac    5640
ccccccagac cggaaacgac ggagcgaaac accgccccaa aggcgggcac ggccccccggg   5700
gcaaccgcag aacacgacca gagacccac cacccaacgc ccgggcgccg ggaaacagca    5760
gacaccccg caacaggcgg gaaacacacc agacgcccaa ccaagggcga ggccgagaca    5820
cacacccacc aggcccaaga caccggacca gaaccaacga aagaggagcg gaccgaagcc    5880
cggacccca gccaaagaaa agcccagggc gacgccccgc acacaacccc caacgaacga    5940
cgcgagggcc agcccagaa aacgggcgc caccccaga gcgggaagag ccgggcgcgg     6000
cagcagagcg ccccaccccg ggagggagag cggccgcgcg gcgaacccaa cgggcgggaa    6060
gaccaagcca aaccacccag ccggaggcgc gccacggaac cagggcaccg cggcgccggc    6120
gggggcgaca acacagcggc gcggcccgac cccgcgaccc agccacccac cgaggagagg    6180
ccccaccccc gccggagagc ggcacacaag cacacccaag caacgccacc cccccacacc    6240
accccggggcc cacagcccag cacggcagcg gaaaggccgg agccgcagac gcagagaggc    6300
cgaacggccc gcagacagca ga                                                6322
```

NUCLEIC ACID AND GENE DERIVED FROM NOVEL HCV STRAIN AND REPLICON-REPLICATING CELL USING SAID GENE

TECHNICAL FIELD

The present invention relates to a nucleic acid and gene derived from a novel fulminant hepatitis C virus strain, an HCV replicon using the gene and a replicon-replicating cell.

BACKGROUND ART

For virus research and research and development of antiviral drugs, an experimental system that allows efficient viral amplification is absolutely essential. Further, when there is a system for amplifying virus by the use of cultured cells or a system for evaluating virus proliferation by the use of cultured cells, virus research and research and development of antiviral drugs show dramatic progress.

Hepatitis C virus (HCV) is a virus belonging to the flavivirus family with a single-stranded (+) sense strand RNA as the genome and is known to cause hepatitis C. Recent studies have revealed that the hepatitis C virus can be classified into many types depending on genotypes or serotypes. According to the method of systematic analysis by Simmonds et al. using nucleotide sequences of HCV strains that is currently the mainstream method for classification of HCV genotypes, HCVs are classified into six types, i.e. genotype 1a, genotype 1b, genotype 2a, genotype 2b, genotype 3a, and genotype 3b, and further each type of them is classified into several subtypes (Simmonds, P. et al., Hepatology (1994) 10, p 1321-1324). At present, the full length genome nucleotide sequences of a plurality of HCV genotypes have been determined (Choo et al., Science, (1989) 244, p 359-362; Kato et al., J. Med. Virol., (1992) p 334-339; Okamoto, H et al., J. Gen. Virol., (1992) 73, p 673-679; Yoshioka et al., Hepatology, (1992) 16, 293-299).

Current major treatment for hepatitis C is performed with interferon-α, interferon-β, and a combination therapy of interferon-α and ribabirin that is a purine nucleoside derivative. However, even when these treatments are performed, the therapeutic effect is observed only in about 60% of all patients who underwent therapy, and more than half of the patients who had the effect relapse when the treatment was stopped. The therapeutic effect of interferon is known to be associated with HCV genotypes and it is said that its effect on genotype 1b is low while its effect on genotype 2a is higher (Mori, S., et al., Biochem. Biophys. Res. Commun., (1992) 183, 334-342).

The development of effective therapeutic drug or prophylactic drug for hepatitis C that has high morbidity in industrial countries and finally leads to a serious result and for which there is presently no causal therapy is an important challenge. Therefore, progress in chemotherapy specific to HCV or vaccine therapy and development of anti-HCV drug are eagerly awaited. As a target for the development of anti-HCV drug, suppression of HCV replication and suppression of cell infection of HCV are conceivable.

Since, until recently, it has been difficult to propagate HCV in a cell culture system as well as to infect cultured cells by HCV and animals that can be infected by HCV and subjected to experiments have been limited only to chimpanzee, researches on mechanism of HCV replication and mechanism of HCV infection have remained difficult. However, HCV subgenomic RNA replicons have recently been created as RNAs that have been derived from HCV and have autonomous replication ability (JP Patent Publication (Kokai) No. 2001-17187 (2001); Lomann et al., Science, (1999) 285, 110-113; Blight et al., Science, (2000) 290, 1972-1974; Friebe et al., (2001) 75, 12047-12057; Ikeda et al., J. Virol., (2002) 76, 2997-3006), thereby allowing the mechanism of HCV replication to be analyzed by the use of cultured cells. These HCV subgenomic RNA replicons are ones in which structural proteins that are present downstream of HCV IRES in the 5' untranslated region of HCV genomic RNA of a clone referred to as Con 1 belonging to genotype 1b are substituted by neomycin-resistant gene and EMCV-IRES linked to the downstream thereof. It has been demonstrated that these replicon RNAs autonomously replicate in Huh7 cells by introducing them into human hepatocarcinoma Huh7 cells and culturing in the presence of neomycin. An evaluation system of HCV replication using this RNA replicon system is considered to become a powerful tool for the development of anti-HCV drug.

It has been reported that, in HCVs different in genotypes, encoded viral proteins also differ, and it is conceivable that full elucidation of the mechanism of HCV replication is difficult only by analyzing the subgenomic RNA replicon derived from genotype 1b HCV. Further, it is assumed that the development of an anti-HCV drug that exerts an effect on various types of HCVs by using only the HCV replication system containing the subgenomic RNA replicon of genotype 1b HCV is particularly difficult because the therapeutic effect of interferon differs depending on HCV genotypes. Accordingly, it is considered that researches on the mechanism of HCV replication and the anti-HCV drug should be conducted by creating HCV RNA replicons of many genotypes.

At present, there are only several lines of clones that can replicate as a replicon in cultured cells. Further, a clone that was cloned from chronic hepatitis and has been confirmed to be infectious to chimpanzees is not necessarily able to replicate as a replicon (Lomann et al., Science, (1999) 285, 110-113). That is, a method for selecting an HCV strain that makes it possible to produce HCV replicon with excellent efficiency of replication as well as with high probability has not yet been found, and when such a selection method of HCV strain is established, the research and development of HCV therapeutic drug is expected to dramatically advance.

For HCV, a vaccine has not been developed at present. One of the reasons for this is that HCV-related proteins that can serve as the vaccine can not be stably produced in a form present in vivo in a large amount. Since HCV-related proteins are expressed in the HCV replicon cells described above (JP Patent Publication (Kokai) No. 2001-17187 (2001)), it is expected that this HCV replicon cells can be used. However, it is necessary to use cells that can be mass-cultured for industrial production of vaccines. From this point of view, Huh7 cells established as the only HCV RNA replicon-replicating cells at present seem to be unsuitable for the vaccine production. For cells suitable for the vaccine production, cells that can be cultured in a very large amount in a suspension culture system such as HeLa cells are conceivable. Furthermore, since the sequence of HCVs differs depending on the genotypes as described above, the vaccine needs to be produced for every genotype. In other words, HCV RNA replicon cells of various genotypes need to be produced using cells suitable for the vaccine production. On the other hand, Huh7 cells are considered not suitable for establishing a cell culture system that allows HCV to autonomously infect and replicate also in the respect that the susceptibility to infection by HCV has not been confirmed. Accordingly, it is thought to be essential to establish a cell culture system that allows HCV to autonomously infect and replicate using other hepatocarcinoma cells.

Moreover, it becomes possible to identify cellular factors necessary for HCV replication by comparing the differences of the mechanism of HCV RNA replicon replication among various kinds of cells, which may be expected to lead to discovery of a novel target for anti-HCV therapeutic drug.

DISCLOSURE OF THE INVENTION

The present invention aims to provide HCV replicon RNA with excellent efficiency of replication with high probability and HCV replicon cells capable of continuously producing HCV proteins in a large amount.

As a result of assiduous research intended to solve the above problems, the present inventors perfected the present invention by discovering that replicon-replicating cells with excellent efficiency of replication with high probability can be obtained by using replicons derived from a HCV strain, JFH2.1 or JFH2.2, from patients with fulminant hepatitis C.

That is, the present invention provides a nucleic acid consisting of a polynucleotide (a), (b), or (c):
(a) a polynucleotide comprising nucleotide sequences shown by SEQ ID NO:1, SEQ ID NO:3, and SEQ ID NO:4;
(b) a polynucleotide comprising nucleotide sequences shown by SEQ ID NO:2, SEQ ID NO:5, and SEQ ID NO:6; and
(c) a polynucleotide that hybridizes to a polynucleotide consisting of a nucleotide sequence complementary to the nucleotide sequence according to the above (a) or (b) under stringent conditions and encodes an HCV proteins,
provided that, if the nucleic acid is a DNA, the nucleotide symbol "u" in the sequence listings shall be replaced with "t".

The present invention also provides the following nucleic acids (1) to (6) as an example of the above nucleic acids.
(1) A nucleic acid consisting of a polynucleotide (a) or (b):
(a) a polynucleotide comprising the nucleotide sequences represented by SEQ ID NO:1; and
(b) a polynucleotide that hybridizes to a polynucleotide consisting of a nucleotide sequence complementary to the nucleotide sequence according to the above (a) under stringent conditions and codes for NS3, NS4A, NS4B, NS5A, and NS5B proteins among HCV proteins,
(2) A nucleic acid consisting of a polynucleotide (a) or (b):
(a) a polynucleotide comprising the nucleotide sequence represented by SEQ ID NO:3; and
(b) a polynucleotide that hybridizes to a polynucleotide consisting of a nucleotide sequence complementary to the nucleotide sequence according to the above (a) under stringent conditions and codes for the 5' untranslated region of HCV genes,
(3) A nucleic acid consisting of a polynucleotide (a) or (b):
(a) a polynucleotide comprising the nucleotide sequence represented by SEQ ID NO:4; and
(b) a polynucleotide that hybridizes to a polynucleotide consisting of a nucleotide sequence complementary to the nucleotide sequence according to the above (a) under stringent conditions and codes for the 3' untranslated region of the HCV genes,
(4) A nucleic acid consisting of a polynucleotide (a) or (b):
(a) a polynucleotide comprising the nucleotide sequence represented by SEQ ID NO:2; and
(b) a polynucleotide that hybridizes to a polynucleotide consisting of a nucleotide sequence complementary to the nucleotide sequence according to the above (a) under stringent conditions and codes for the NS3, NS4A, NS4B, NS5A, and NS5B proteins among the HCV proteins,
(5) A nucleic acid consisting of a polynucleotide (a) or (b):
(a) a polynucleotide comprising the nucleotide sequence represented by SEQ ID NO:5; and
(b) a polynucleotide that hybridizes to a polynucleotide consisting of a nucleotide sequence complementary to the nucleotide sequence according to the above (a) under stringent conditions and codes for the 5' untranslated region of HCV genes,
(6) A nucleic acid consisting of a polynucleotide (a) or (b):
(a) a polynucleotide comprising the nucleotide sequence represented by SEQ ID NO:6; and
(b) a polynucleotide that hybridizes to a polynucleotide consisting of a nucleotide sequence complementary to the nucleotide sequence according to the above (a) under stringent conditions and codes for the 3' untranslated region of HCV genes,
provided that, if the nucleic acid is a DNA in any of the above (1) to (6), the nucleotide symbol "u" in the sequence listing shall be replaced by "t".

The present invention also provides genes consisting of the above-described nucleic acids and polypeptides encoded by the genes.

The present invention also provides a replicon RNA consisting of an RNA (a) or (b):
(a) An RNA comprising the nucleotide sequences shown by SEQ ID NO:1, SEQ ID NO:3, and SEQ ID NO:4
(b) An RNA comprising the nucleotide sequences shown by SEQ ID NO:2, SEQ ID NO:5, and SEQ ID NO:6

In addition, the replicon RNA may further comprise an IRES sequence and a selection marker gene or a reporter gene.

The present invention also provides a replicon RNA consisting of an RNA (a) or (b):
(a) An RNA comprising the nucleotide sequence shown by SEQ ID NO:7 or SEQ ID NO:8
(b) An RNA that hybridizes to an RNA consisting of a nucleotide sequence complementary to the nucleotide sequence according to the above (a) under stringent conditions and has autonomous replication ability The present invention also provides a method to create replicon-replicating cells by introducing the replicon RNA into appropriate cells as well as the replicon-replicating cells created by the method. Cells for use in the replicon-replicating cells include human liver-derived cells, human cervix-derived cells, or human embryonic kidney-derived cells, and more specifically, Huh7 cells, HepG2 cells, IMY-N9 cells, HeLa cells, or 293 cells.

The present invention also provides a method for screening substances to stimulate or suppress replication of hepatitis C virus, which includes culturing the replicon-replicating cells in the presence of a test substance and detecting replication of the replicon RNA in the resulting culture.

The present invention also provides a method for increasing replication efficiency of replicon RNA of hepatitis C virus, which includes performing a process at least once in which replicated replicon RNA is obtained from the replicon-replicating cells and the replicated replicon RNA obtained is introduced into other cells to create new replicon-replicating cells. In the method, it is desirable that the replication efficiency is increased at least twice as high as the replication efficiency of the replicon RNA that has been introduced into the replicon-replicating cells.

The present invention also provides a method for producing hepatitis C virus replicon RNA with a higher efficiency of replication, which includes performing a process at least once in which replicated replicon RNA is obtained from the replicon-replicating cells and the replicated replicon RNA obtained is introduced into cells different from the replicon-replicating cells to create new replicon-replicating cells and obtaining replicated replicon RNA from finally obtained replicon-replicating cells.

Further, the present invention also provides a method for producing hepatitis C virus replicon RNA with a higher efficiency of replication, which includes detecting nucleotide or amino acid mutation between the replicon RNA with a higher efficiency of replication produced by the above-described method and the replicon RNA introduced into the replicon-replicating cells initially and introducing the detected nucleotide or amino acid mutation into replicon RNA intending to enhance replication efficiency.

When the novel HCV RNA gene of the present invention is used, the replicon RNA and replicon-replicating cells with excellent efficiency of replication with high probability can be obtained. These replicon-replicating cells can be utilized for a culture system to continuously produce RNA derived from HCV and HCV proteins. Further, the replicon-replicating cells can also be utilized for a test system to screen various substances that exert an effect on replication of HCV or translation of HCV proteins.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Figure 1:
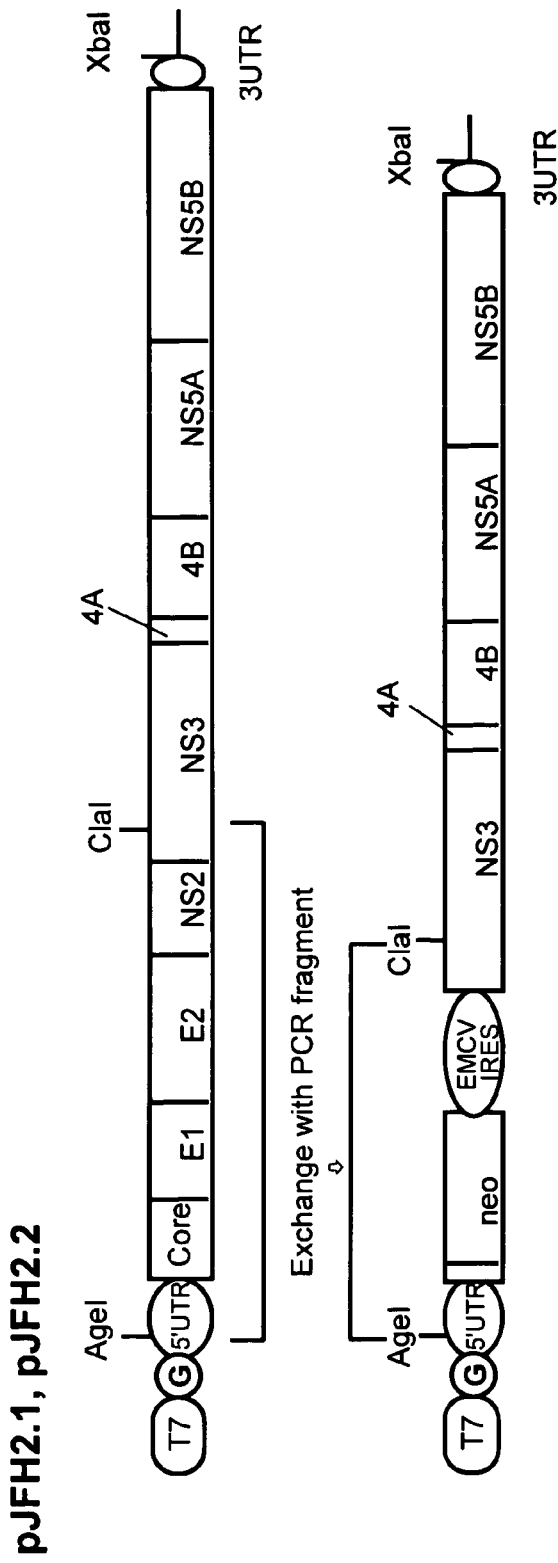
FIG. 1 is a diagram showing structures of plasmid DNAs, pJFH-2.1 and pJFH-2.2 (upper row) and plasmid DNAs, pSGREP-JFH2.1 and pSGREP-JFH2.2 (lower row)

The present specification encompasses the contents described in the specification of Japanese Patent Application No. 2003-329082, on which the priority of the present application is based.

BEST MODE FOR CARRYING OUT THE INVENTION

Hereinafter, the present invention is described in detail.
1. Nucleic Acid, Gene, and Replicon RNA Derived from HCV According to the Present Invention The genome of hepatitis C virus (HCV) is a (+) strand single stranded RNA consisting of approximately 9600 nucleotides. This genomic RNA comprises the 5' untranslated region (also referred to as 5' NTR or 5' UTR), the translated region consisting of structural and nonstructural regions, and the 3' untranslated region (also referred to as 3' NTR or 3' UTR). Structural proteins of HCV are encoded in the structural region and a plurality of nonstructural proteins are encoded in the nonstructural region.

These structural proteins (Core, E1, and E2) and nonstructural proteins (NS2, NS3, NS4A, NS4B, NS5A, and NS5B) of HCV are translated as a continuous polyprotein from the translated region and then undergo limited proteolysis by proteases to be produced as free forms. Of these structural proteins and nonstructural proteins (i.e. viral proteins of HCV), Core is the core protein, E1 and E2 are the envelope proteins, and the nonstructural proteins are proteins that are involved in the replication of the virus itself. It is known that NS2 has metalloprotease activity and that NS3 has serine protease activity (one-third on the N-terminal side) and helicase activity (two-thirds on the C-terminal side). Further, NS4A is a cofactor for the protease activity of NS3, and NS5B has also been reported to have RNA-dependent RNA polymerase activity.

The present inventors constructed RNA that has excellent efficiency of replication with high probability and can replicate autonomously in cells such as Huh7 cells using HCV genome selected based not on commonly used genotypic classification of HCV but on a criterion that HCV has been isolated from patients with fulminant hepatitis.

In the present specification, RNA that has autonomous replication ability and has been constructed by modifying viral genome of natural HCV is referred to as "replicon RNA" or "RNA replicon".

In the present specification, "gene" means "nucleic acid responsible for specific function or information involved in life activity" among nucleic acids and includes both RNA and DNA. In addition, the nucleic acid or gene may be either single-stranded (cDNA, cRNA, etc.) or double-stranded and either naturally occurring or artificially synthesized. Further, it may be partially modified or may be a derivative. Although the nucleotide sequences in sequence listings are shown by RNA for convenience, the nucleotide symbol "U" shall be replaced by "T" when the gene involved is DNA.

In the present invention, "fulminant hepatitis" means hepatitis that presents encephalopathy of stage II or greater developed within 8 weeks after symptom onset and a prothrombin time of not more than 40%, and is classified into acute form in which encephalopathy is developed within 10 days and sub-acute form in which encephalopathy is developed thenafter. "Hepatitis C virus originating from patients with fulminant hepatitis" means HCV isolated from patients who presented this symptom of "fulminant hepatitis". In the present invention, "hepatitis C virus originating from patients with fulminant hepatitis" or "HCV of fulminant strain" includes not only virus having HCV genomic RNA of natural origin but also virus having genomic RNA in which artificial modification was added to the HCV genomic sequence of natural origin. Specific examples of fulminant strains of HCVs include viruses such as JFH-1 strain (JP Patent Publication (Kokai) No. 2002-171978 (2002)), JFH-2.1 strain, and JFH-2.2 strain.

In the specification of the present application, "5' untranslated region (5' NTR or 5' UTR)", "sequence coding for NS3 protein, NS4A protein, NS4B protein, NS5A protein, and NS5B protein", "sequence coding for Core protein (Core region or C region)", "sequence coding for E1 protein (E1 region)", "sequence coding for E2 protein (E2 region)", "sequence coding for N2 protein (NS2 region)", "sequence coding for NS3 protein (NS3 region)", "sequence coding for NS4A protein (NS4A region)", "sequence coding for NS4B protein (NS4B region)", "sequence coding for NS5A protein (NS5A region)", "sequence coding for NS5B protein (NS5B region)", and "3' untranslated region (3' NTR or 3' UTR)" as well as other specific regions or sites shall be determined based on the full-length genomic RNAs encoding the whole genomic region of JFH-2.1 and JFH-2.2 strains that are hepatitis C viruses originating from patients with fulminant hepatitis C or polynucleotides comprising nucleotide sequences (SEQ ID NOS:1 to 6, respectively) of their partial genomic RNAs (JFH-2.1 and JFH-2.2 clones).

Specifically, as to JFH-2.1 clone, when RNA sequence of a specific HCV is aligned against the nucleotide sequences shown by SEQ ID NOS:1, 3, and 4, the nucleotide sequence shown by SEQ ID NO:3 is the "5'untranslated region" of the RNA, the nucleotide sequence shown by SEQ ID NO:1 is the "sequence coding for NS3 protein, NS4A protein, NS4B protein, NS5A protein, and NS5B protein", in which the sequence of nucleotide nos. 1 to 1893 is the "sequence coding for NS3 protein", the sequence of nucleotide nos. 1894 to 2055 is the "sequence coding for NS4A protein", the sequence of nucleotide nos. 2056 to 2838 is the "sequence coding for NS4B protein", the sequence of nucleotide nos. 2839 to 4236 is the "sequence coding for NS5A protein", the sequence of nucleotide nos. 4273 to 6012 is the "sequence coding for NS5B protein", and the nucleotide sequence shown by SEQ ID NO:4 is the "3'untranslated region".

As to JFH-2.2 clone, when RNA sequence of a specific HCV is aligned against the nucleotide sequences shown by SEQ ID NOS:2, 5, and 6, the nucleotide sequence shown by SEQ ID NO:5 is the "5'untranslated region" of the RNA, the nucleotide sequence shown by SEQ ID NO:2 is the "sequence coding for NS3 protein, NS4A protein, NS4B protein, NS5A protein, and NS5B protein", in which the sequence of nucleotide nos. 1 to 1893 is the "sequence coding for NS3 protein", the sequence of nucleotide nos. 1894 to 2055 is the "sequence coding for NS4A protein", the sequence of nucleotide nos. 2056 to 2838 is the "sequence coding for NS4B protein", the sequence of nucleotide nos. 2839 to 4236 is the "sequence coding for NS5A protein", the sequence of nucleotide nos. 4273 to 6012 is the "sequence coding for NS5B protein", and the nucleotide sequence shown by SEQ ID NO:6 is the "3'untranslated region".

For the genes according to the present invention, in addition to the polynucleotides comprising the nucleotide sequences represented by SEQ ID NOS:1 to 6 described above, polynucleotides that hybridize to the genes under stringent conditions are included in the genes of the present invention as long as those encode the above-described desirable proteins. Here, the stringent conditions are such conditions that hybridization is performed at 60 degrees C. in the presence of 6×SSC (the composition of 1× concentration of SSC solution consists of 150 mmol/l sodium chloride and 15 mmol/l sodium citrate) and then washed with 1×SSC containing 0.1% SDS at 68 degrees C. For a method of the hybridization, colony hybridization method, plaque hybridization method, Southern hybridization method, or the like can be used, and these methods can be carried out according to the description in, for example, Molecular Cloning, A laboratory manual, 20001, Eds., Sambrook, J. & Russell, D W. Cold Spring Harbor Laboratory Press.

In the nucleic acids or genes of the present invention, gap, addition, deletion, substitution, and the like may be present in their sequences as long as those encode the above-described desirable proteins. Specifically, in the nucleotide sequences shown by SEQ ID NOS:1 to 6, as long as those encode the desirable proteins even when those are polynucleotides consisting of nucleotide sequences with deletion, substitution, or addition of one or a plurality of nucleotides, that is, 1 to 50, preferably 1 to 30, more preferably 1 to 10, further more preferably 1 to 6, and most preferably one to several (2 to 5) nucleotides, in other words, as long as a polynucleotide comprising the nucleotide sequence represented by SEQ ID NO:1 or 2 is one that encodes NS3, NS4A, NS4B, NS5A, and NS5B proteins among HCV proteins, a polynucleotide comprising the nucleotide sequence represented by SEQ ID NO:3 or 5 is one that encodes the 5' untranslated region of the HCV genes, and a polynucleotide comprising the nucleotide sequence represented by SEQ ID NO:4 or 6 is one that encodes the 3' untranslated region of the HCV genes, those polynucleotides are included in the nucleic acids or genes of the present invention ("a polynucleotide comprising the nucleotide sequence" is sometimes expressed as "a nucleotide sequence comprising the nucleotide sequence").

Further, the above-described "specific HCV" is not limited to JFH-2.1 strain and JFH-2.2 strain but includes virus strains that are derivatives thereof.

One embodiment of the HCV replicon RNA according to the present invention is a replicon RNA consisting of a nucleotide sequence that contains at least the 5' untranslated region, the sequence coding for NS3 protein, NS4A protein, NS4B protein, NS5A protein, and NS5B protein, and the 3' untranslated region that are present on the genomic RNA of a hepatitis C virus originating from fulminant hepatitis. This replicon RNA may further contain one IRES sequence, and may furthermore contain one selection marker gene or reporter gene therein. Still further, this replicon RNA may contain sequences encoding viral proteins other than NS3, NS4A, NS4B, NS5A, or NS5B protein that are present on genomic RNAs of hepatitis C viruses other than JFH2.1 and JFH2.2.

Another exemplary embodiment of the HCV replicon RNA according to the present invention is a replicon RNA comprising a polynucleotide that contains the 5' untranslated region having the nucleotide sequence shown by SEQ ID NO:3, at least one selection marker gene or reporter gene, at least one IRES sequence, the nucleotide sequence coding for NS3 protein, NS4A protein, NS4B protein, NS5A protein, and NS5B protein on HCV genomic RNA shown by SEQ ID NO:1, and the 3' untranslated region having the nucleotide sequence shown by SEQ ID NO:4, or a polynucleotide that contains the 5' untranslated region having the nucleotide sequence shown by SEQ ID NO:5, at least one selection marker gene and/or reporter gene, at least one IRES sequence, the nucleotide sequence coding for NS3 protein, NS4A protein, NS4B protein, NS5A protein, and NS5B protein on HCV genomic RNA shown by SEQ ID NO:2, and the 3' untranslated region having the nucleotide sequence shown by SEQ ID NO:6.

The replicon RNA according to the present invention preferably has the 5' untranslated region on HCV genomic RNA of SEQ ID NO:3 or 5 on the far most 5' side and the 3' untranslated region on HCV genomic RNA of SEQ ID NO:4 or 6 on the far most 3' side. The selection marker gene or reporter gene may be linked upstream of the IRES sequence, may be linked upstream or downstream of the "sequence coding for NS3 protein, NS4A protein, NS4B protein, NS5A protein, and NS5B protein", or may be inserted in the "sequence coding for NS3 protein, NS4A protein, NS4B protein, NS5A protein, and NS5B protein".

The replicon RNA according to the present invention more preferably has the 5' untranslated region on HCV genomic RNA of SEQ ID NO:3 or 5, has the selection marker gene or the reporter gene, the IRES sequence, and the "sequence coding for NS3 protein, NS4A protein, NS4B protein, NS5A protein, and NS5B protein" in this order in the downstream of the 5' untranslated region, and further has the 3' untranslated region on genomic RNA of HCV originating from patients with fulminant hepatitis on the far most 3' side.

Still another exemplary embodiment of the HCV replicon RNA according to the present invention is a replicon RNA consisting of RNA having the nucleotide sequence shown by SEQ ID NO:7 or 8. Further, a nucleic acid that hybridizes to the gene consisting of the nucleotide sequence shown by SEQ ID NO:7 or 8 under stringent conditions is also included. Furthermore, in this nucleotide sequence shown by SEQ ID NO:7 or 8, a replicon RNA having the nucleotide sequence with deletion, substitution, or addition of one or a plurality of nucleotides, that is, 1 to 50, preferably 1 to 30, more preferably 1 to 10, further more preferably 1 to 6, and most preferably one to several (2 to 5) nucleotides and having autonomous replication ability is also included in the scope of the present invention as the exemplary embodiment. "Having autonomous replication ability" in the present invention means that when a replicon RNA is introduced into cells, the replicon RNA is capable of replication of the full-length replicon RNA itself in the cells. Although not intending to limit, this autonomous replication ability can be confirmed, for example, by transfecting the replicon RNA into Huh7 cells, culturing the Huh 7 cells, extracting RNA from the cells in the resulting culture, performing Northern blot hybridization with the use of a probe that can specifically detect the transfected replicon RNA, and detecting the presence of the replicon RNA. Specific procedures to confirm the autonomous replication ability can be carried out according to the descriptions of measurement of colony formation ability, determination of HCV protein expression, detection of replicon RNA, and the like that are described in the examples of the present specification.

The replicon RNA according to the present invention may include RNA containing an arbitrary foreign gene desired to be expressed in the cells that are transfected with replicon RNA. The foreign gene may be linked downstream of the 5' untranslated region, may be linked upstream or downstream of the selection marker gene or the reporter gene, may be linked upstream or downstream of the "sequence coding for NS3 protein, NS4A protein, NS4B protein, NS5A protein, and NS5B protein", or may be inserted in the "sequence coding for NS3 protein, NS4A protein, NS4B protein, NS5A protein, and NS5B protein". The replicon RNA containing the foreign gene is able to express the protein encoded by the foreign gene when translated in the transfected cells. Accordingly, the replicon RNA containing the foreign gene can also be desirably used when production of a specific gene product in cells is aimed as in the case of gene therapy and the like.

"Selection marker gene" in the present invention means a gene that can provide selectivity to cells such that only the cells expressing the gene are selected. A common example of the selection marker gene includes an antibiotic-resistant gene. Examples of preferred selection marker genes in the present invention include neomycin-resistant gene, thymidine kinase gene, kanamycin-resistant gene, pyrithiamine-resistant gene, adenylyltransferase gene, Zeocin-resistant gene, puromycin-resistant gene, and the like, in which neomycin-resistant gene and thymidine kinase gene are preferred, and neomycin-resistant gene is further preferred. It should be noted that the selection marker gene in the present invention is not limited to these.

Further, in the present invention, "reporter gene" means a marker gene that encodes a gene product used as an indicator of the expression of the gene. A common example of the reporter gene includes the structural gene of an enzyme that catalyzes a luminescent reaction or color reaction. Examples of preferred reporter genes in the present invention include chloramphenicol acetyltransferase gene from transposon Tn9, β-glucuronidase or β-galactosidase gene from E. coli, luciferase gene, green fluorescent protein gene, aequorin gene from jelly fish, secreted placental alkaline phosphatase (SEAP) gene, and the like. It should be noted that the reporter gene in the present invention is not limited to these.

Either one of the above selection marker gene and the reporter gene may be contained in the replicon RNA, or both of them may be contained therein.

"IRES sequence" in the present invention means an internal ribosome binding site that allows a ribosome to bind internally in RNA to initiate translation. Although not limited to the following, preferred example of IRES sequences in the present invention include EMCV IRES (internal ribosome binding site of encephalomyocarditis virus), FMDV IRES, HCV IRES, and the like, in which EMCV IRES and HCV IRES are more preferred and EMCV IRES is most preferred.

The replicon RNA according to the present invention may further include a ribozyme. The ribozyme is inserted so as to link a selection marker gene, reporter gene, or foreign gene that is located on the 5' side in the replicon RNA to the IRES sequence and the "sequence coding for NS3 protein, NS4A protein, NS4B protein, NS5A protein, and NS5B protein" that are located on the 3' side from the former, thereby allowing both of them to be separated by cleavage due to self-cleavage activity of the ribozyme.

In the replicon RNA according to the present invention, the above-described selection marker gene, reporter gene, sequence coding for viral proteins on genomic RNA of hepatitis C virus originating from patients with fulminant hepatitis, foreign gene, and the like are linked so as to be translated from the replicon RNA in a correct reading frame. Among these sequences, the sequence coding for the proteins may also be linked individually to one another via protease cleavage sites and the like such that each protein is separated by a protease after expressing as a fusion protein which is fused to the polyprotein translated from the "sequence coding for NS3 protein, NS4A protein, NS4B protein, NS5A protein, and NS5B protein" of hepatitis C virus originating from patients with fulminant hepatitis.

2. Creation of Replicon RNA According to the Present Invention

The HCV replicon RNA according to the present invention can be created with the use of arbitrary gene engineering technique known to persons skilled in the art. Although not intending to limit, the HCV replicon RNA can be created, for example, by the following method.

First, a DNA clone is created by inserting DNAs corresponding to RNAs of the NS3 protein, NS4A protein, NS4B protein, NS5A protein, and NS5B protein (SEQ ID NO:1 or 2) and the 3' untranslated region (SEQ ID NO:4 or 6) into a cloning vector by a conventional method. On the other hand, the 5' untranslated region (SEQ ID NO:3 or 5) is inserted downstream of RNA promoter to create DNA clone. Here, "DNA corresponding to RNA" means DNA consisting of the nucleotide sequence in which U (uracil) in the nucleotide sequence of RNA is replaced by T (thymine). The RNA promoter is preferably one that is contained in a plasmid clone. Although not intending to limit, preferred RNA promoters include T7 RNA promoter, SP6 RNA promoter, and T3 RNA promoter, and T7 RNA promoter is particularly desirable.

Next, for the DNA clone of the 5' untranslated region that has been constructed, a selection marker gene or a reporter gene is inserted, for example, downstream of the 5' untranslated region, and an IRES sequence is inserted downstream thereof. Further, the DNA having the nucleotide sequence shown by SEQ ID NO:1 or 2 and the DNA having the nucleotide sequence shown by SEQ ID NO:4 or 6 are linked downstream of the IRES sequence in this order.

Then, RNA is synthesized by an RNA polymerase using the DNA clone constructed as described above as a template. The RNA synthesis can be initiated from the 5' untranslated region and the IRES sequence according to a conventional method. When the template DNA is a plasmid clone, the above-described DNA region linked downstream of an RNA promoter is cut out from the plasmid clone by a restriction enzyme, and RNA can also be synthesized using the DNA fragment as a template. In addition, the 3' end of the synthesized RNA desirably coincides with the 3' untranslated region of virus genome RNA, and it is desired that other sequences are not added or deleted. The RNA thus synthesized is the replicon RNA according to the present invention.

3. Creatio of Replicon-Replicating Cells Transfected with HCV Replicon RNA According to the Preset Invention Cells that continuously replicate replicon RNA can be obtained by introducing the replicon RNA created as described above into cells that allows replication of the replicon RNA. In the present specification, the cells that continuously amplify the replicon RNA are referred to as "replicon-replicating cells".

Although any cells can be used for the cells to be transfected with the replicon RNA if the cells can be subcultured, the cells are preferably eukaryotic cells, more preferably human liver-derived cells, human cervix-derived cells, or human embryonic kidney-derived cells, and further more preferably Huh7 cells, HepG2 cells, IMY-N9 cells, HeLa cells, or 293 cells. For these cells, cells that are commercially available or obtained from cell bank may be used, or a cell line established from arbitrary cells (for example, cancer cells or stem cells) may be used.

For the above cells, it is desirable to use cells that can be mass-cultured when mass production of HCV proteins as in the case of vaccine production is intended. From such a viewpoint, cells other than Huh7 cells are desirable.

The introduction of the replicon RNA into cells can be performed by using any technique known to persons skilled in the art. These introduction techniques include, for example, electroporation, particle gun method, lipofection method, calcium phosphate method, microinjection method, DEAE-Sepharose method, and the like, and the method by electroporation is particularly preferred.

As for replicon RNA, the target replicon RNA may be introduced into cells either alone or in a mixture with other nucleic acids. When the amount of the replicon RNA is desired to be varied while keeping the amount of introduced RNA constant, a mixture of the target replicon RNA with total cellular RNA extracted from the cells to be transfected may be used for introduction into the cells. The amount of the replicon RNA used for introduction into the cells may be determined depending on an introduction method to be used, and an amount preferably ranging from 1 picogram to 100 micrograms and more preferably ranging from 10 picograms to 10 micrograms is used.

When the replicon RNA containing a selection marker gene or a reporter gene is used for introduction into cells, cells that have been transfected with the replicon RNA and are continuously replicating the replicon RNA can be selected by making use of the expression of the selection marker gene or the reporter gene. Specifically, for example, these cells that have been treated with the replicon RNA for its intracellular introduction may be cultured in a culture medium that allows selection by the expression of the selection marker gene or the reporter gene.

As an example, when neomycin-resistant gene is contained in the replicon RNA as the selection marker gene, cells that have been treated with the replicon RNA for its intracellular introduction are seeded in a culture dish, cultured for 16 to 24 hours, and then G418 (neomycin) at a concentration of 0.05 mg/ml to 3.0 mg/ml is added in the culture dish. After that, the culture is continued while changing the culture medium twice a week. After culturing preferably for 10 days to 40 days, more preferably 14 days to 28 days from the time of seeding, the cells that have been transfected with the replicon RNA and are continuously replicating the replicon RNA can be selected as a colony by staining the viable cells with crystal violet.

From the formed colony, cells can be cloned by a conventional method. The thus obtained cell clone that continuously replicates the target replicon RNA is referred to as "replicon-replicating cell clone" in the present specification.

As for the established cell clone, it is desirable to confirm that the target replicon RNA is actually replicated continuously by carrying out detection of the replicon RNA replicated from the transfected replicon RNA in the cell clone, determination of the presence or absence of integration of the selection marker gene or the reporter gene in the transfected replicon RNA into the host genomic DNA, and confirmation of expression of HCV proteins.

The detection of the replicon RNA replicated from the transfected replicon RNA in the cell clone (hereinafter, referred to as "replicated replicon RNA" for convenience in the present specification) may be carried out by any RNA detection method known to persons skilled in the art, and for example, the replicon RNA can be detected by carrying out Northern hybridization method for total RNA extracted from the cell clone using a DNA fragment specific to the transfected replicon RNA as a probe.

The determination of integration of the selection marker gene or the reporter gene in the transfected replicon RNA into the host genomic DNA can be carried out, for example, although not intending to be limiting, by performing PCR to amplify at least part of the selection marker gene or the reporter gene for the host genomic DNA extracted from the cell clone and determining the presence or absence of the amplified product. Although the cell clone in which the amplified product has been detected is considered to have introduced the selection marker gene or the reporter gene into the host genome, there is a possibility that the replicon RNA itself may not be continuously replicated within the cells. In this case, it is possible to determine whether or not the replicon RNA is continuously replicated by the experiment to confirm expression of HCV proteins as shown below.

The confirmation of expression of HCV proteins can be performed, for example, by allowing an antibody against HCV protein that should be expressed from the transfected replicon RNA to react with proteins extracted from the cell clone. This method can be carried out by any method of protein detection known to persons skilled in the art, and can be specifically performed, for example, by blotting a protein sample extracted from the cell clone to a nitrocellulose membrane, allowing an anti-HCV protein antibody (for example, anti-NS3 specific antibody or an anti-serum collected from patients with hepatitis C) to react with the protein sample, and further detecting the anti-HCV protein antibody. When HCV protein is detected in the proteins extracted from the cell clone, the cell clone can be considered to be expressing HCV protein by continuous replication of the replicon RNA derived from HCV.

As described above, the cell clone that has been confirmed to be continuously replicating the target replicon RNA (replicon-replicating cell clone) can be obtained. Further, in the present invention, the replicon RNA can be obtained from this replicon-replicating cells by any method known to persons skilled in the art, for example, by extracting RNA and separating the replicon RNA from the RNA extract by electrophoresis and so forth. The present invention also provides such a method of producing the replicon RNA. Further, the replicon-replicating cells according to the present invention can be desirably used for production of HCV proteins. Any person skilled in the art can perform the production of HCV proteins from the replicon-replicating cells according to a conventional method. Specifically, for example, the replicon-replicating cells are cultured, and the proteins can be obtained from the resulting culture (cultured cells and culture medium included) using a conventional method.

Furthermore, when the replicon-replicating cells according to the present invention continuously replicate the replicon RNA containing a foreign gene, the protein encoded by the foreign gene can be obtained by allowing expression of the protein using the replicon-replicating cells. Specifically, for example, the replicon-replicating cells are cultured, proteins are extracted from the resulting culture (cultured cells and culture medium included) by a conventional method, and further, the protein encoded by the foreign gene can be selectively obtained from the extracted proteins by detection with the use of an antibody against the target protein and so forth.

4. Introduction of Mutation to Enhance Replication Efficiency into HCV replicon RNA According to the Present Invention In the replicon RNA produced by replication in the replicon-replicating cells (replicated replicon RNA) according to the present invention, mutations that enhance the replication efficiency occur quite frequently. Such mutations seem to be adaptive mutations.

In the present invention, taking advantage of this fact, mutations to enhance the replication efficiency can be introduced into the replicon RNA according to the present invention with high frequency.

Specifically, a process in which a first replicated replicon RNA is obtained from first replicon-replicating cells (preferably replicon-replicating cells transfected with the replicon RNA according to the present invention) by extraction and the like and then the first replicated replicon RNA is further reintroduced into different cells to create second replicon-replicating cells is performed repetitively at least once, preferably once to ten times, more preferably once to 5 times, and further more preferably once to twice, thereby allowing mutations that enhance replication efficiency to be introduced into the replicon RNA with high frequency.

Although any cells can be used for the cells that are retransfected with the replicated replicon RNA, the cells are preferably cells derived from the same biospecies as the cells initially transfected with the replicon RNA, more preferably cells derived from the same tissue derived from the same biospecies as the cells initially transfected with the replicon RNA, and further more preferably cells of the same cell line as the cells initially transfected with the replicon RNA.

Thus, in the present invention, the replicon RNA in which mutations to enhance replication efficiency have been introduced can be produced with the use of the above method. That is, the process in which the first replicated replicon RNA is obtained in the first place from the first replicon-replicating cells (the replicon-replicating cells transfected with the replicon RNA according to the present invention) by extraction and the like and then the first replicated replicon RNA is further reintroduced into different cells to create the second replicon-replicating cells is performed repetitively at least once, preferably once to ten times, more preferably once to 5 times, and further more preferably once to twice, and subsequently the replicated replicon RNA is acquired from the final replicon-replicating cells obtained at the end of the repetitive processes by extraction and the like, thereby allowing the replicon RNA that is enhanced in replication efficiency to be produced.

In the present invention, the replication efficiency of the replicon RNA can be increased at least two-fold, preferably 10- to 100-fold, and more preferably 100- to 10000-fold by the method described above.

With respect to the replicon RNA with a higher efficiency of replication that has been produced in this way, it is desirable that the nucleotide sequence of the replicon RNA is determined by a known method in which cDNA is obtained by reverse transcription PCR, then it is subjected to nucleotide sequence determination, and so forth. Further, adaptive mutations can be identified by comparing the determined nucleotide sequence or amino acid sequence encoded by the nucleotide sequence to the nucleotide sequence of the replicon RNA initially introduced into cells. For the adaptive mutation to enhance the replication efficiency, particularly nonsynonymous substitution that causes amino acid mutation in viral protein encoded in the replicon RNA is desirable.

The present invention also provides a method of producing the replicon RNA of hepatitis C virus that is enhanced in the replication efficiency by introducing adaptive mutations identified as above into the replicon RNA by a conventional method.

The replicon RNA with a higher efficiency of replication that has been produced as described above can be used for producing a large amount of the replicon RNA.

The replication efficiency of the replicon RNA according to the present invention can be determined according to a method known to persons skilled in the art, for example, by the following method.

For example, Huh7 cells are transfected with 0.0001, 0.0003, 0.001, 0.003, 0.01, 0.03, 0.1, 0.3, and 1.0 microgram of the replicon RNA respectively and subjected to selection culture with G418 for 21 days in a manner similar to the experimental procedures described above, and then the number of colony formation (colony number) is measured. By comparing the amount of the introduced RNA and the number of colony formation, a range of the introduction amounts of the replicon RNA where the colony formation increases dose-dependently is determined, and the value obtained by dividing the number of colony formation within the range by the amount of the introduced RNA is defined as colony formation rate per one microgram. This calculation equation is as shown below. Colony formation rate [(colony forming unit; CFU)/microgram]=number of colony formation [piece]/amount of introduced RNA [microgram]

The colony formation rate thus calculated is defined as a value indicating the replication efficiency of the transfected replicon RNA. That is, the higher the colony formation rate, the higher the replication efficiency of the replicon RNA is.

Further, the replication efficiency of the replicon RNA can also be expressed by colony formation ability that is shown by the copy number of transfected replicon RNA per one colony formed. That is, the colony formation ability can be calculated according to the following calculation equation. Colony formation ability=copy number of transfected replicon RNA [copy]/number of colony formation [piece]

5. OTHER EMBODIMENTS OF THE PRESENT INVENTION

The replicon RNA-replicating cells according to the present invention can also be used, for example, as a test system for screening of substances that stimulate or suppress the replication of hepatitis C virus. Specifically, for example, the replicon-replicating cells are cultured in the presence of a test substance, replication of the replicon RNA in the resulting culture is detected, and whether or not the test substance stimulates or suppresses the replication of the replicon RNA is considered, thereby making it possible to screen substances that stimulate or suppress the replication of hepatitis C virus. In this case, the detection of replication of the replicon RNA in the resulting culture may be carried out either by detection of the amount or the presence or absence of the replicon RNA in RNA extracted from the replicon RNA-replicating cells or by detection of the amount or the presence or absence of HCV proteins contained in proteins in the culture or in the replicon RNA-replicating cells present in the culture.

Such a test system can be used for production or evaluation of therapeutic agent or diagnostic agent for hepatitis C virus infection. Specifically, the following examples can be listed.

(1) Screening for Substances to Suppress Proliferation of HCV

Substances to suppress proliferation of HCV include, for example, organic compounds that exert an effect directly or indirectly on the proliferation of HCV or antisense oligonucleotides and the like that exert an effect directly or indirectly on the proliferation of HCV or translation of HCV proteins by hybridizing to a target sequence of HCV genome or complementary strand thereof.

(2) Evaluation of Various Substances Having an Anti-Virus Action in Cell Culture The various substances include substances obtained by the use of rational drug design or high throughput screening (for example, isolated and purified enzymes) and the like.

(3) Identification of Novel Targets for Attack to Treat Patients Infected with HCV The replicon-replicating cells according to the present invention can be used to identify, for example, host cellular proteins that play an important role in the proliferation of HCV virus.

(4) Evaluation of Potential for Acquisition of Resistance to Drug and the Like for HCV Virus and Identification of Mutations Involved in the Resistance (5) Production of Viral Proteins as Antigens Usable for Development, Production, and Evaluation of Diagnostic Agent or Therapeutic Agent for Hepatitis C Virus Infection The present invention is explained in more concrete terms based on the following examples and drawings.

EXAMPLE 1

Replication of Replicon RNA
1. Construction of Expression Vector

DNAs corresponding to the whole regions of virus genomes of hepatitis C viruses, JFH-2.1 strain and JFH-2.2 strain, isolated from patients with fulminant hepatitis were obtained from JFH-2.1 and JFH-2.2 clones containing the full-genome-length cDNAs of the virus strains, and synthetic DNA of T7 RNA promoter sequence was attached to the 5' end of each clone and then inserted into a plasmid, pUC19 plasmid. Hereinafter, the thus-constructed plasmid DNAs are referred to as pJFH-2.1 and pJFH-2.2, respectively. It should be noted that the creation of the above-described JFH-2.1 and JFH-2.2 clones was carried out according to a published report (Lehmann et al., Science, (1999)).

The structures of the thus-constructed plasmid DNAs, pJFH-2.1 and pJFH-2.2, are shown in the upper row of FIG. 1. "T7" indicates T7 RNA promoter, and "G" indicates dGTP inserted upstream of the 5' ends of JFH-2.1 and JFH-2.2 and downstream of the 3' ends of T7 RNA promoter sequence. The range from "5'NTR" to "3'NTR" represents DNA corresponding to the whole genomic region of hepatitis C virus.

Next, part of the structural regions and the nonstructural regions of the plasmid DNAs, pJFH-2.1 and pJFH-2.2, were substituted by neomycin-resistant gene (neo; also referred to as neomycin phosphotransferase gene) and EMCV-IRES (internal ribosome binding site of encephalomyocarditis virus) to construct plasmid DNAs, pSGREP-JFH2.1 and pSGREP-JFH2.2, respectively (the lower row of FIG. 1). This construction procedure was carried out according to the published report (Lehmann et al., Science, (1999)). Specifically, the plasmids, pJFH2.1 and pJFH2.2, were cleaved by the restriction enzymes, AgeI and ClaI; to the cleavage site, the sequence extending from the 5' NTR to Core region derived from each of pJFH2.1 and pJFH2.2 and the neomycin-resistant gene derived from the expression vector pRSV5NEO are ligated by PCR amplification; the fragment cleaved by the restriction enzymes, AgII and PmeI, and the sequence extending from EMCV IRES to NS3 region were ligated by PCR amplification; and the fragment cleaved by the restriction enzymes, PmeI and ClaI, was inserted and ligated.

2. Creation of Replicon RNA

In order to create a template DNA used for synthesis of replicon RNA, the expression vectors, pSGREP-JFH2.1 and pSGREP-JFH2.2, constructed as described above were cleaved by a restriction enzyme XbaI, respectively. Then, 10 to 20 µg of these XbaI cleavage fragments were incubated, respectively, with 20 U of Mung Bean Nuclease for 30 min at 30 degrees C. (total volume of the reaction solution, 50 µl) for further treatment. The Mung Bean Nuclease is an enzyme that catalyzes a reaction to selectively degrade single-stranded portion in double- stranded DNA. In general, when synthesis of RNA is carried out using the fragment cleaved by XbaI as it is as a template, a replicon RNA additionally attached, on the 3' end, with four nucleotides CUGA that is part of the recognition sequence of XbaI is synthesized. Accordingly, in the present example, the four nucleotides CTAG were removed from the fragment cleaved by XbaI by treating the fragment cleaved by XbaI with the Mung Bean Nuclease. Then, the fragment cleaved by XbaI from which the four nucleotides CTAG had been removed was purified from the solution containing the fragment cleaved by XbaI after the treatment with the Mung Bean Nuclease by protein removal treatment according to a conventional method, and this purified fragment was used as a template DNA.

Next, RNA was synthesized in vitro from this template DNA. For the RNA synthesis, MEGA script available from Ambion, Inc. was used. A reaction was carried out in 20 µl of the reaction solution containing 0.5 to 1.0 µg of the template DNA for 3 hours to 16 hours at 37 degrees C.

After the synthesis of RNA, DNAse (2 U) was added to the reaction solution and reacted for 15 min at 37 degrees C., and then RNA extraction was carried out by acidic phenol to remove the template DNA. The RNAs (replicon RNAs) that were thus synthesized from the above-described template DNAs derived from pSGREP-JFH2.1 and pSGREP-JFH2.2 were designated as rSGREP-JFH2.1 and rSGREP-JFH2.2, respectively. The nucleotide sequences of these replicon RNAs are shown by SEQ ID NO:7 and FIG. 1 for rSGREP-JFH2.1 and by SEQ ID NO:8 and FIG. 1 for rSGREP-JFH2.2.

EXAMPLE 2

Establishment of Replicon-Replicating Cell Clones

Figure 2:
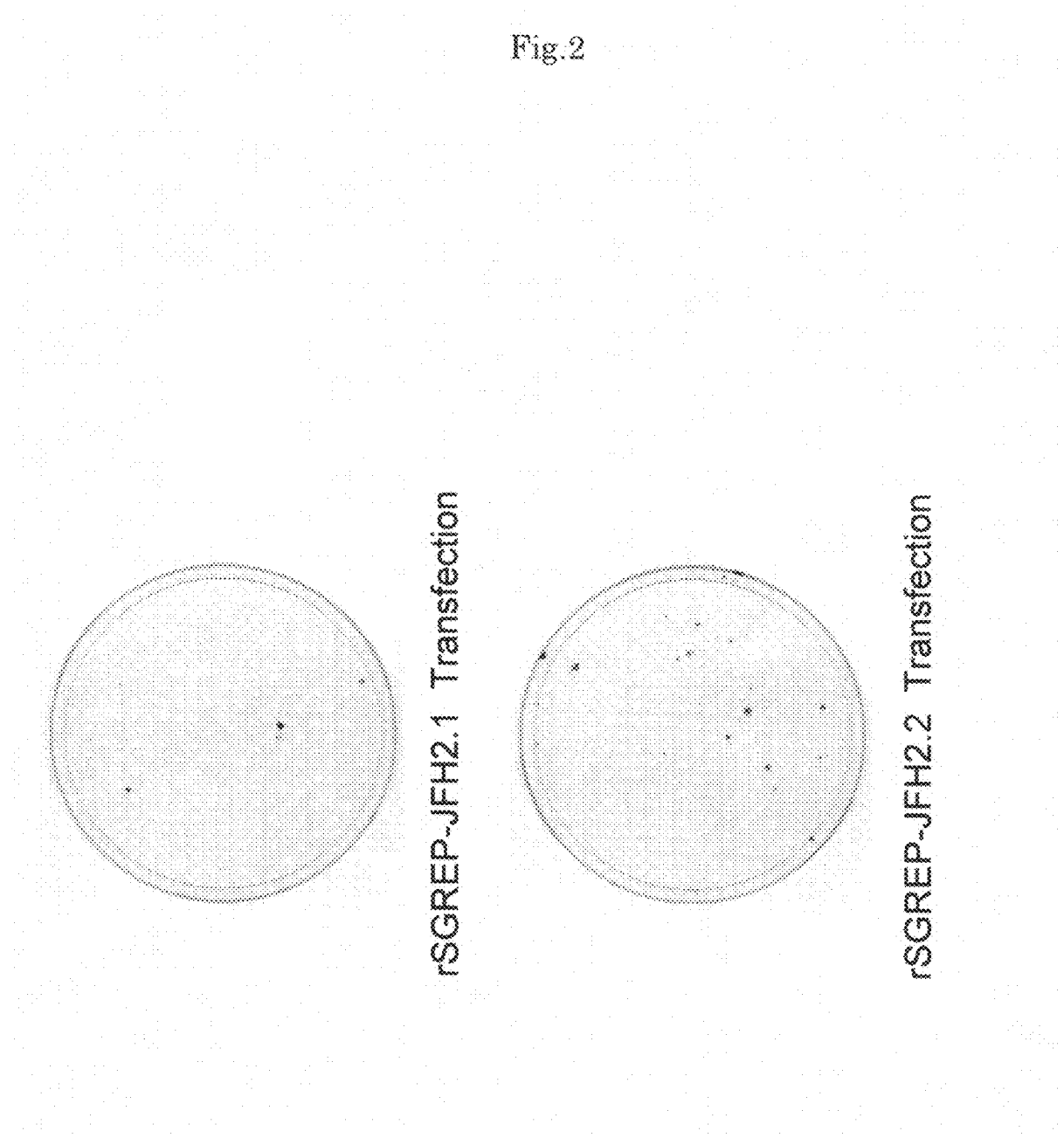
FIG. 2 is a picture image showing colony formation of cells transfected with rSGREP-JFH2.1 or rSGREP-JFH2.2.

For each of the synthetic replicon RNAs, rSGREP-JFH2.1 and rSGREP-JFH2.2 created in the example 1, 0.01 ng to 10 µg of the replicon RNA was mixed with total cellular RNA extracted from Huh7 cells to adjust the total RNA amount to 10 µg. Subsequently, the mixed RNA was introduced into Huh7 cells by electroporation. The Huh7 cells subjected to the treatment with electroporation were seeded in culture dishes and cultured for 16 hours to 24 hours, followed by addition of G418 (neomycin) into the dishes at various concentrations. Then, the culture was continued while changing the culture medium twice a week. After culturing for 21 days from the time of seeding, viable cells were stained with crystal violet. As the result, colony formation was confirmed as shown in FIG. 2.

For the cells that were transfected with rSGREP-JFH2.1 and rSGREP-JFH2.2 and showed colony formation, colonies of viable cells were further cloned from the culture dishes after culturing for 21 days, and the cultures were continued. A plurality of lines of cloned cells could be established by this cloning of colonies.

All printed publications, patents, and patent applications cited in the present specification are incorporated as they are by reference into the present specification.

INDUSTRIAL APPLICABILITY

HCV replicon RNA having excellent efficiency of replication with high probability can be created by using genes derived from HCV strains, JFH2.1 or JFH2.2, originating from patients with fulminant hepatitis C according to the present invention. Replicon-replicating cells transfected with the replicon RNA can be used as a culture system to continuously produce RNA derived from HCV and HCV proteins. Further, the replicon-replicating cells can be used as a test system to screen various substances that exert an effect on replication of HCV and/or translation of HCV proteins.

Sequence Listing Free Text

SEQ ID NO:7-Description of artificial sequence: JFH2.1 replicon RNA

SEQ ID NO:8-Description of artificial sequence: JFH2.2 replicon RNA

The invention claimed is:

1. An isolated nucleic acid comprising:
(a) the nucleotide sequences shown by the 5' untranslated region of SEQ ID NO:3, the nucleotide sequence encoding NS3, NS4A, NS4B, NS5A and NS5B proteins from nucleotides 1-6012 of SEQ ID NO:1 and the 3' untranslated region of SEQ ID NO:4; or
(b) an entire nucleotide sequence according to (a) one or a plurality of nucleotide substitutions which functions as an RNA replicon, wherein said nucleotide substitutions reflect degeneracy in the genetic code;

provided that, if the nucleic acid is a DNA, the nucleotide symbol "u" in the sequence listings shall be replaced with "t".

2. A replicon RNA comprising, in order, the nucleotide sequences shown by the 5'untranslated region of SEQ ID NO:3, the nucleotide sequence encoding NS3, NS4A, NS4B, NS5A and NS5B proteins from nucleotides 1-6012 of SEQ ID NO:1 and the 3' untranslated region of SEQ ID NO:4.

3. The replicon RNA according to claim 2, further comprising an IRES sequence.

4. The replicon RNA according to claim 3, further comprising a selection marker gene or a reporter gene.

5. A replicon RNA consisting of (a) or (b):
 (a) the nucleotide sequence shown by SEQ ID NO:7; or
 (b) an entire nucleotide sequence according to (a) one or a plurality of nucleotide substitutions which has an autonomous replication ability, wherein said nucleotide substitutions reflect degeneracy in the genetic code.

6. A replicon-replicating cell created by introducing the replicon RNA according to any one of claims 2 to 5 into isolated cells.

7. The replicon-replicating cell according to claim 6, wherein the isolated cells are human liver-derived cells, human cervix-derived cells, or human embryonic kidney-derived cells.

8. A method for screening a substance to stimulate or suppress replication of hepatitis C virus, comprising culturing the replicon-replicating cell according to claim 6 in the presence of a test substance and detecting replication of a replicon RNA in the resulting culture.

9. The replicon RNA according to claim 3, further comprising a selection marker gene.

* * * * *